United States Patent
Oruganti et al.

(10) Patent No.: US 11,390,583 B2
(45) Date of Patent: Jul. 19, 2022

(54) PROCESS FOR PREPARATION OF SIPONIMOD, ITS SALTS AND SOLID STATE FORMS THEREOF

(71) Applicant: DR. REDDY'S LABORATORIES LIMITED, Hyderabad (IN)

(72) Inventors: Srinivas Oruganti, Hyderabad (IN); Krishnarao Chintada, Srikakulam (IN); Bhaskar Kandagatla, Hyderabad (IN); Raju Cheerlavancha, Karimnagar (IN); Vamsi Krishna Mudapaka, Bhadrachalam (IN); Rajasekhar Voguri, Hyderabad (IN); Rajesh Thipparaboina, Mancherial (IN); Satyanarayana Thirunahari, Hyderabad (IN)

(73) Assignee: DR. REDDY'S LABORATORIES LIMITED, Hyderabad (IN)

( * ) Notice: Subject to any disclaimer, the term of this patent is extended or adjusted under 35 U.S.C. 154(b) by 69 days.

(21) Appl. No.: 16/651,214

(22) PCT Filed: Sep. 26, 2018

(86) PCT No.: PCT/IB2018/057424
§ 371 (c)(1),
(2) Date: Mar. 26, 2020

(87) PCT Pub. No.: WO2019/064184
PCT Pub. Date: Apr. 4, 2019

(65) Prior Publication Data
US 2020/0290961 A1    Sep. 17, 2020

(30) Foreign Application Priority Data

Sep. 27, 2017  (IN) .............................. 201741034238
Oct. 12, 2017  (IN) .............................. 201741036303
Mar. 2, 2018   (IN) .............................. 201841007886
Apr. 12, 2018  (IN) .............................. 201841014059
May 11, 2018   (IN) .............................. 201841017715

(51) Int. Cl.
C07D 205/04   (2006.01)
C07D 209/48   (2006.01)

(52) U.S. Cl.
CPC ......... C07D 205/04 (2013.01); C07D 209/48 (2013.01); C07B 2200/13 (2013.01)

(58) Field of Classification Search
CPC .. C07D 209/48; C07D 205/04; C07B 2200/13
See application file for complete search history.

(56) References Cited

U.S. PATENT DOCUMENTS

| 7,939,519 | B2 | 5/2011 | Pan et al. |
| 8,173,634 | B2 | 5/2012 | Liu et al. |
| 8,486,930 | B2 | 7/2013 | De La Cruz et al. |
| 2015/0175536 | A1 | 6/2015 | Ciszewski |

FOREIGN PATENT DOCUMENTS

WO    2013113915 A1    8/2013

OTHER PUBLICATIONS

International Search Report dated Jan. 16, 2019, for corresponding International Patent Application No. PCT/IB2018/057424.
Written Opinion dated Jan. 16, 2019, for corresponding International Patent Application No. PCT/IB2018/057424.

*Primary Examiner* — Kamal A Saeed
(74) *Attorney, Agent, or Firm* — Pergament & Cepeda LLP; Milagros A. Cepeda; Edward D. Pergament

(57) ABSTRACT

The present application provides process for preparation of siponimod, intermediates of siponimod, salts of siponimod, polymorphic forms and solid dispersions of siponimod and its salts thereof. The present application specifically provides crystalline polymorphic forms of siponimod base, siponimod hemifumarate and other salts and pharmaceutical compositions thereof. Also provided are solid dispersions of siponimod hemifumarate and pharmaceutical compositions containing them.

7 Claims, 10 Drawing Sheets

PROCESS FOR PREPARATION OF SIPONIMOD, ITS SALTS AND SOLID STATE FORMS THEREOF

CROSS-REFERENCE TO RELATED APPLICATIONS

This application is a National Stage Application under 35 U.S.C. § 371 of PCT International Application No. PCT/IB2018/057424, filed Sep. 26, 2018, which takes priority from Indian Provisional Application Numbers IN 201741034238, filed Sep. 27, 2017, IN 201741036303, filed Oct. 12, 2017, IN 201841007886, filed Mar. 2, 2018, IN 201841014059 filed Apr. 12, 2018 and IN 201841017715, filed May 11, 2018, all of which are herein incorporated by reference in their entireties.

FIELD OF THE INVENTION

The present application relates to processes for preparation of Siponimod, its intermediates, siponimod salts, solid state forms of siponimod salts, and pharmaceutical compositions thereof.

BACKGROUND OF THE INVENTION

The drug compound having the adopted name Siponimod, has a chemical name (E)-1-(4-(1-(((4-cyclohexyl-3-(trifluoromethyl)benzyl)oxy)-imino)ethyl)-2-ethylbenzyl)-azetidine-3-carboxylic acid, and is represented by the structure of formula I.

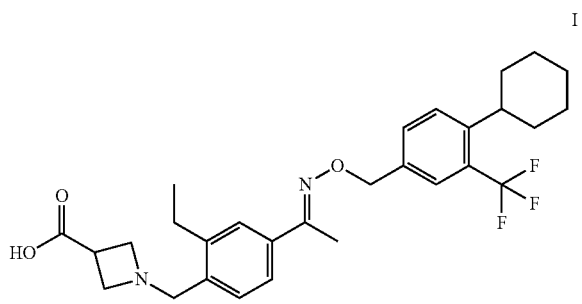 [SMILES: CCc1cc(/C(C)=N/OCc2ccc(C3CCCCC3)c(C(F)(F)F)c2)ccc1CN1CC(C(=O)O)C1]

Siponimod is an investigational selective sphingosine-1-phosphate receptor modulator drug currently in phase III clinical trials for the therapy of secondary progressive multiple sclerosis.

Siponimod base, its synthetic process and its pharmaceutical compositions are described in U.S. Pat. No. 7,939,519 B2 (US '519). The process described in US '519 is schematically represented below:

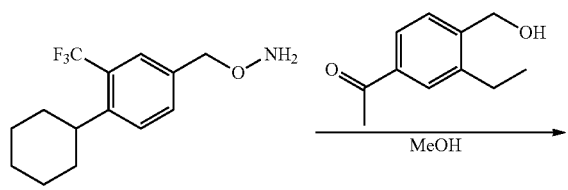

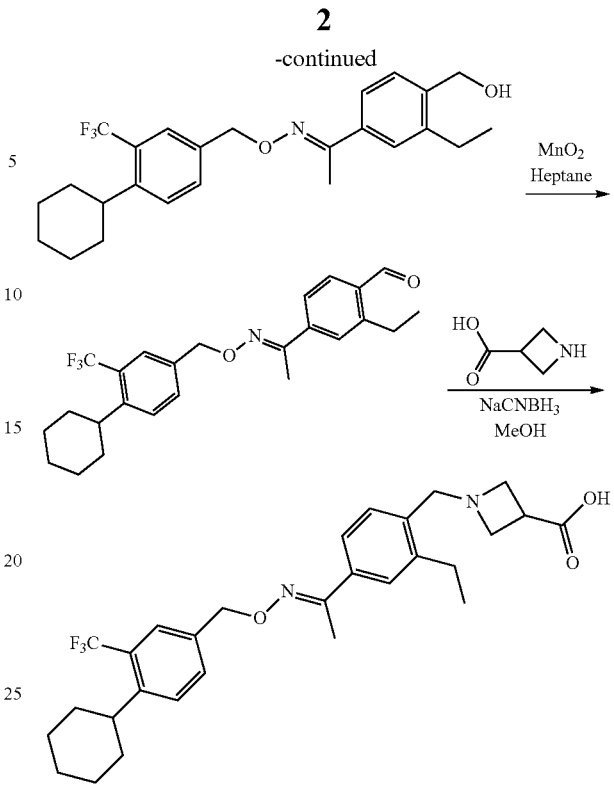

U.S. Pat. No. 8,173,634 B2 (US '634) describes crystalline polymorphic form A of siponimod base and pharmaceutical compositions thereof.

U.S. Pat. No. 8,486,930 B2 (US '930) describes siponimod hydrochloride salt, siponimod malate salt, siponimod oxalate salt, siponimod tartrate salt and their crystalline polymorphic forms thereof.

US patent application No. 20150175536 A1 (US '536) describes Siponimod hemifumarate salt, crystalline forms of Siponimod hemifumarate salt and their pharmaceutical compositions.

New salts, new polymorphic forms and solvates of a pharmaceutical product can provide materials having better bioavailability, desirable processing properties, such as ease of handling, ease of processing, storage stability, and ease of purification or as desirable intermediate crystal forms that facilitate conversion to other salts or polymorphic forms. For at least these reasons there remains a need to provide commercially viable and advantageous processes for preparation of Siponimod, its salts and solid state forms of siponimod and its salts.

SUMMARY OF THE INVENTION

The present application generally relates to process for preparation of Siponimod, pharmaceutically acceptable salts of siponimod and solid state forms thereof.

In a first aspect the present application provides a compound of Formula V and its salts

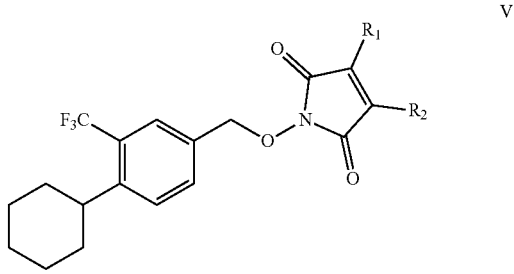

wherein $R_1$ and $R_2$ each independently represents hydrogen, alkyl, halogen, nitro or $R_1$ and $R_2$ together form a 5 to 7 membered ring.

In a second aspect the present application provides a process for preparation of compound of formula V, comprising, reacting a compound of formula VI with a compound of formula VII in presence of a suitable base.

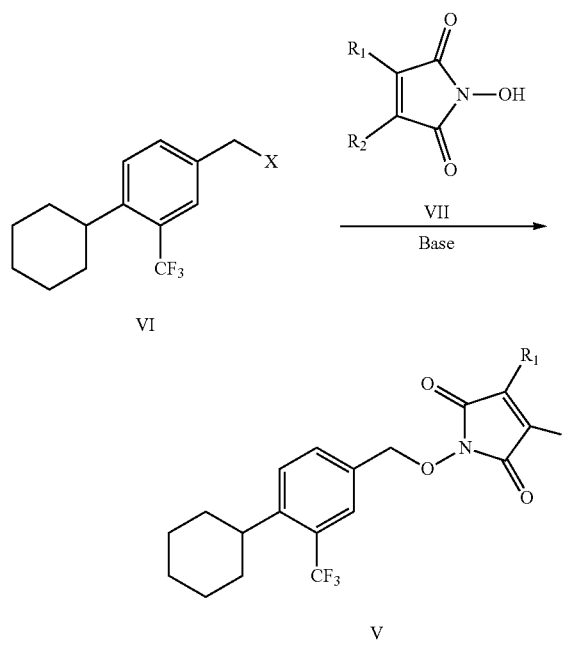

Where in X represents a hydrogen atom or a halogen atom; $R_1$ and $R_2$ each independently represents hydrogen, alkyl, halogen, nitro or $R_1$ and $R_2$ together form a 5 to 7 membered ring.

In a third aspect the present application provides use of compound of formula V or a salt thereof, prepared by the process described in the present application, for the preparation of Siponimod and its slats.

In a fourth aspect the present application provides a process for preparation of Siponimod of formula I or a pharmaceutically acceptable salt thereof, comprising:

a) reacting a compound of formula VI with a compound of formula VII in presence of a suitable base to get a compound of formula V

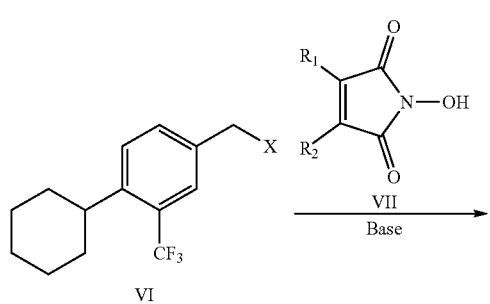

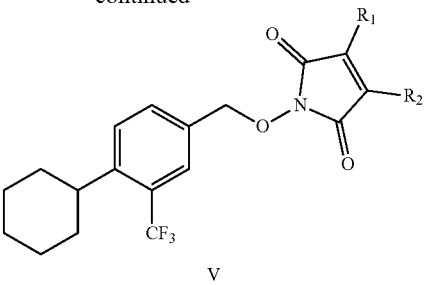

b) reacting the compound of formula V with a suitable amine to form a compound of formula IV

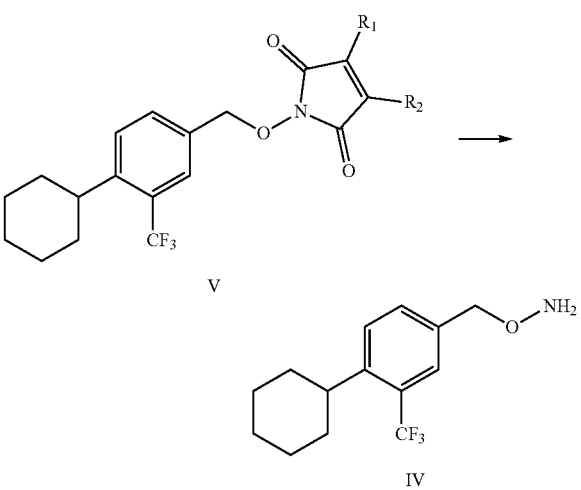

c) reacting the compound of formula IV with 1-(3-ethyl-4-(hydroxymethyl)phenyl)ethan-1-one of formula XII to form a compound of formula III

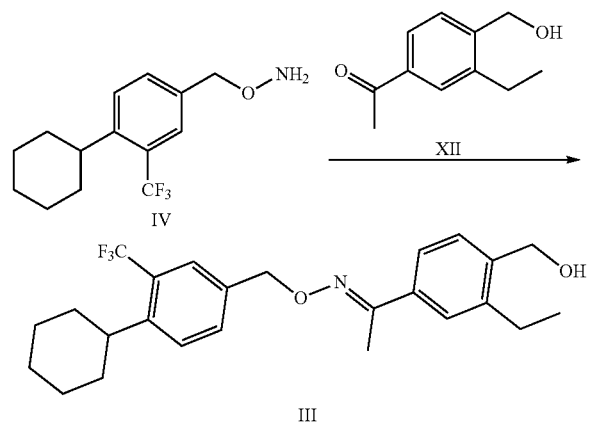

d) oxidizing the compound of formula III using a suitable oxidizing agent to form a compound of formula II

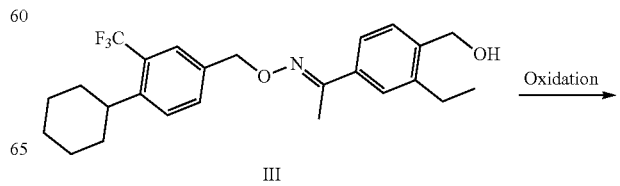

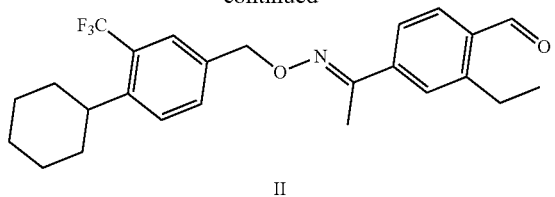

II e) reacting the compound of formula II with azetidine-3-carboxylic acid to form Siponimod of formula I.

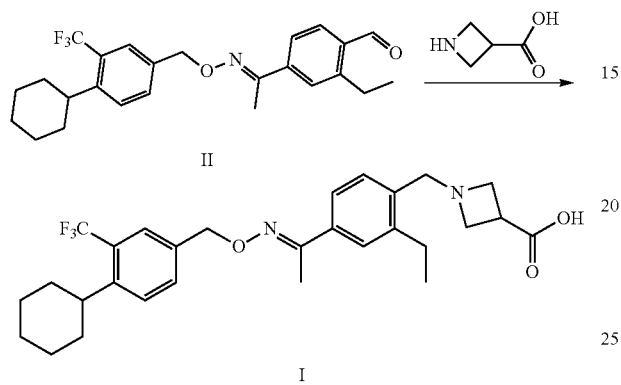

I f) optionally, converting Siponimod into its pharmaceutically acceptable salt.

In a fifth aspect the present application provides a process for preparation of compound of formula V-A, comprising:

a) Reacting a compound of formula XI with cyclohexanone to form a compound of formula X

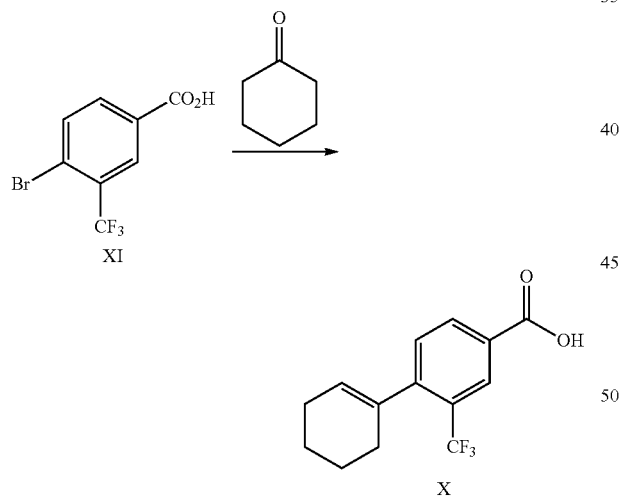

b) Hydrogenating the compound of formula X in presence of suitable catalyst to form a compound of formula IX

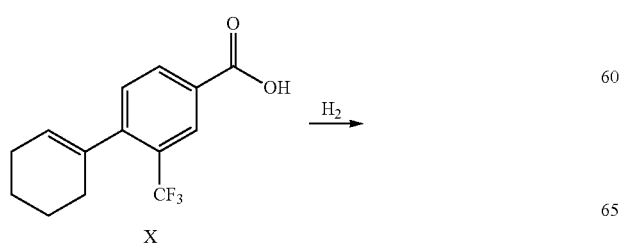

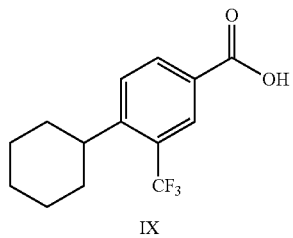

IX c) Reducing the compound of formula IX using a suitable reducing agent to form a compound of formula VIII

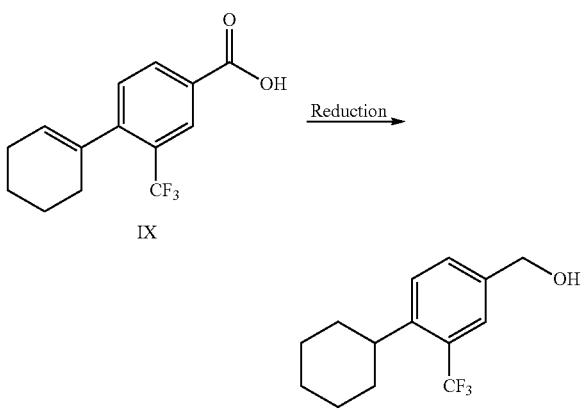

VIII d) reacting the compound of formula VIII with a brominating agent to form a compound of formula VI-A

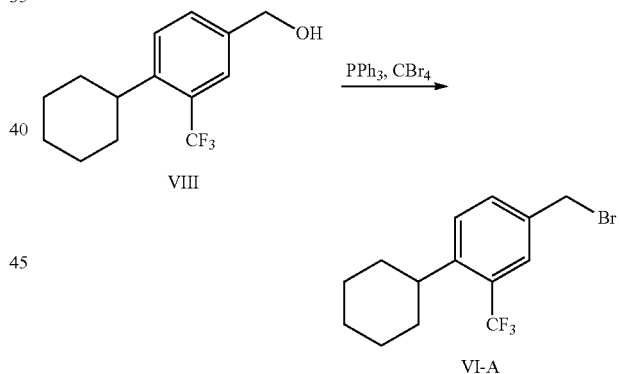

VI-A e) reacting a compound of formula VI-A with 2-hydroxyisoindoline-1,3-dione in presence of a suitable base to get a compound of formula V-A

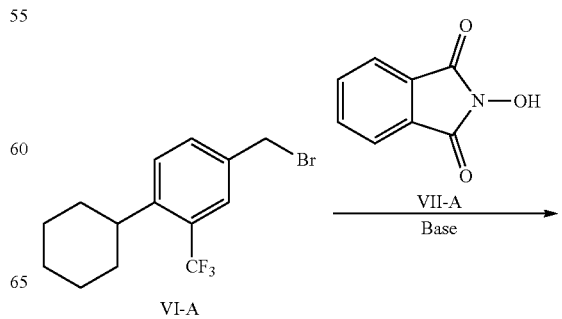

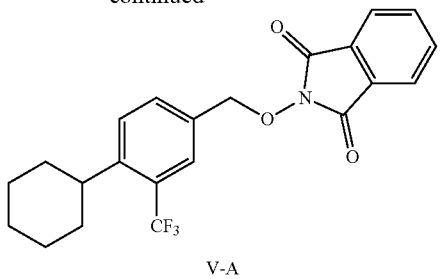

V-A

In a sixth aspect the present application provides a process for preparation of Siponimod hemifumarate salt.

In a seventh aspect, the present application provides a process for preparing crystalline form A of Siponimod hemifumarate, comprising:
a) providing a solution of Siponimod hemifumarate in a solvent or a mixture of two or more solvents;
b) adding an anti-solvent the solution of Siponimod hemifumarate obtained in step a); and
c) isolating crystalline form A of Siponimod hemifumarate.

In an eighth aspect, the present application provides a crystalline Form SHF1 of Siponimod hemifumarate, characterized by a PXRD pattern comprising the peak at about 7.52±0.2° 2θ.

In a ninth aspect, the present application provides a process for the preparation of crystalline Form SHF1 of Siponimod hemifumarate, comprising,
(a) suspending Siponimod hemifumarate in water,
(b) heating the suspension of step (a),
(c) isolating the solid, and
(d) drying the solid to obtain crystalline Form SHF1 of Siponimod hemifumarate.

In a tenth aspect, the present application provides a process for the preparation of crystalline Form SHF1 of Siponimod hemifumarate, characterized by a PXRD pattern comprising the peak at about 7.52±0.2° 2θ, comprising:
(e) providing a mixture of Siponimod hemifumarate and water,
(f) heating the mixture of step (a),
(g) adding an organic solvent to the mixture, and
(h) isolating and drying the solid to obtain crystalline Form SHF1 of Siponimod hemifumarate.

In an eleventh aspect, the present application provides a crystalline Form SHF2 of Siponimod hemifumarate, characterized by a PXRD pattern comprising the peaks at about 5.38 and 8.13±0.2° 2θ.

In a twelfth aspect, the present application provides a process for the preparation of crystalline Form SHF2 of Siponimod hemifumarate, comprising,
(a) providing a mixture of Siponimod hemifumarate and 1,4-dioxane,
(b) stirring the mixture of step (a), and
(c) isolating the crystalline Form SHF2 of Siponimod hemifumarate.

In thirteenth aspect, the present application provides a crystalline Form SF1 of Siponimod monofumarate, characterized by a PXRD pattern comprising the peaks at about 11.62, 12.24, 13.52 and 16.70±0.2° 2θ.

In a fourteenth aspect, the present application provides a process for the preparation of crystalline Form SF1 of Siponimod monofumarate, comprising,
(a) providing a mixture of Siponimod base and an organic solvent,
(b) adding fumaric acid to the mixture of step (a), and
(c) isolating the crystalline Form SF1 of Siponimod monofumarate.

In a fifteenth aspect, the present application provides Siponimod L-proline co-crystal.

In a sixteenth aspect, the present application provides a process for preparation of Siponimod hemifumarate L-proline co-crystal, comprising,
(a) providing a mixture of Siponimod base, fumaric acid and L-proline in a solvent or solvent mixture thereof,
(b) stirring and heating the mixture of step (a), and
(c) isolating the Siponimod hemifumarate L-proline co-crystal.

In a seventeenth aspect, the present application provides use of the crystalline forms of Siponimod hemifumarate to improve the purity of Siponimod hemifumarate.

In an eighteenth aspect, the present application provides a pharmaceutical composition comprising any of the crystalline forms of Siponimod hemifumarate and at least one pharmaceutically acceptable carrier.

In a nineteenth aspect, the present application provides pharmaceutical composition comprising amorphous In a twentieth aspect, the present application provides amorphous form of Siponimod hemifumarate.

In a twenty first aspect, the present application provides amorphous form of Siponimod hemifumarate characterized by powder X-ray diffraction (PXRD) substantially as illustrated in FIG. 1.

In a twenty second aspect, the present application provides a process for preparing amorphous form of Siponimod hemifumarate which comprises;
a) providing a solution of Siponimod hemifumarate in a solvent or a mixture of two or more solvents;
b) removing solvent from the solution of Siponimod hemifumarate obtained in step a); and
c) recovering amorphous form of Siponimod hemifumarate.

In a twenty third aspect, the present application provides pharmaceutical composition comprising amorphous Siponimod hemifumarate and one or more pharmaceutically acceptable excipients.

In a twenty fourth aspect, the present application provides a solid dispersion comprising Siponimod hemifumarate and one or more pharmaceutically acceptable carrier.

In a twenty fifth aspect, the present application provides a process for preparing an amorphous solid dispersion comprising siponimod hemifumarate and one or more pharmaceutically acceptable carriers, the process comprising;
a) providing a solution comprising Siponimod hemifumarate and one or more pharmaceutically acceptable excipients,
b) removing solvent from the solution obtained in step (a), and
c) recovering an amorphous solid dispersion comprising Siponimod hemifumarate and one or more pharmaceutically acceptable excipient.

In a twenty sixth aspect, the present application provides a pharmaceutical composition comprising any one of Siponimod hemifumarate solid dispersion of the present invention and a pharmaceutically acceptable carrier.

In a twenty seventh aspect, the present application provides, Siponimod di p-Toluolyl-L-tartrate, Siponimod dibenzoyl-D-tartrate, and Siponimod isethionate.

In a twenty eighth aspect, the present application provides use of these salts and their crystalline forms for the preparation of Siponimod free base, Siponimod hemifumarate, other slats of Siponimod and solid state forms thereof.

In a twenty ninth aspect, the present application provides pharmaceutical compositions comprising any one, or a combination thereof, the above described Siponimod salts and crystalline forms, and at least one pharmaceutically acceptable excipient.

DETAILED DESCRIPTION

Figure 1:
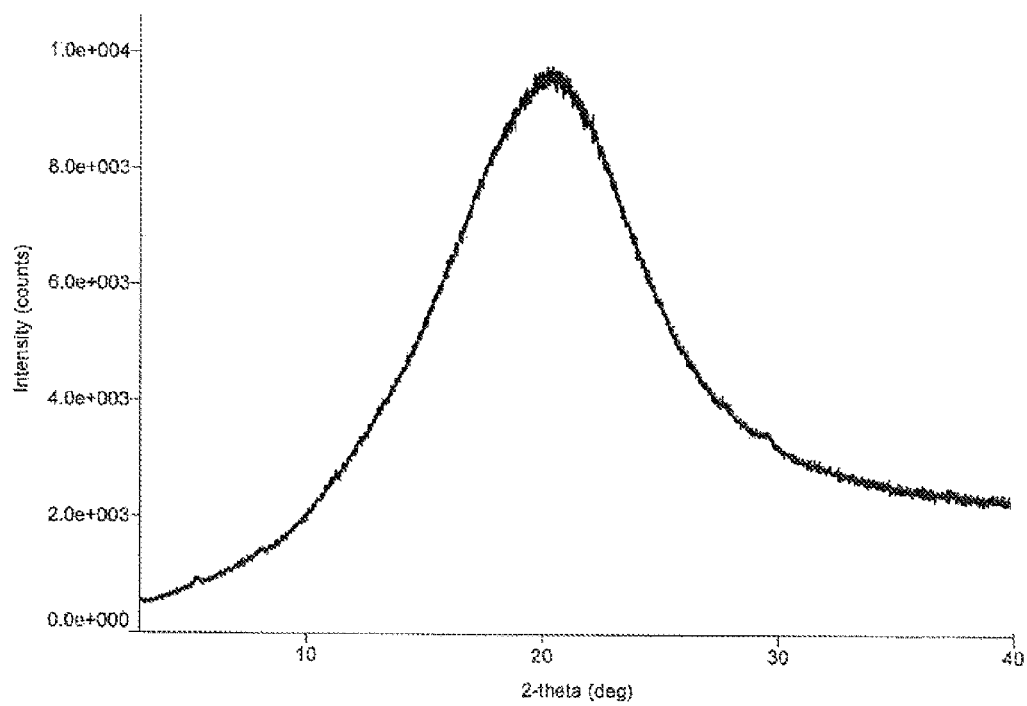
FIG. 1 is powder X-ray power diffraction ("PXRD") pattern of an amorphous form of Siponimod hemifumarate prepared according to Example 10.

The present application generally relates process for preparation of Siponimod, its intermediates and pharmaceutically acceptable salts thereof.

In a first aspect the present application provides a compound of Formula V and its salts

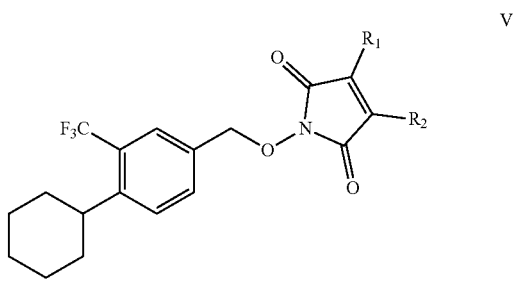

wherein
$R_1$ and $R_2$ each independently represents hydrogen, alkyl, halogen, nitro or $R_1$ and $R_2$ together form a 5 to 7 membered ring.

In a second aspect the present application provides a process for preparation of compound of formula V, comprising, reacting a compound of formula VI with a compound of formula VII in presence of a suitable base.

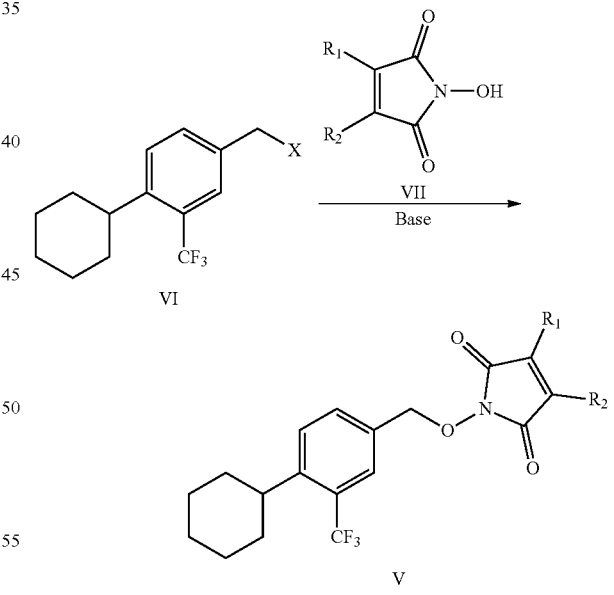

Wherein
X represents a hydrogen or hydroxy or a halogen atom;
$R_1$ and $R_2$ each independently represents hydrogen, alkyl, halogen, nitro or $R_1$ and $R_2$ together form a 5 to 7 membered ring.

The process involves reaction of compound of formula VI with a compound of formula VII in presence of a suitable base such as triethylamine or diisopropyl ethylamine, and a suitable solvent such as N,N-dimethylformamide or N,N-dimethylacetamide. The compound of formula VI can be prepared by the process described in this application or any of the processes described in the art.

The compound of formula VI, the solvent, the base and he compound of formula VII are mixed and the resulted mixture may be stirred for about 10 minutes to about 10 hours at a temperature of about 30° C. to about 100° C.

After completion of the reaction the reaction mixture is added to water and the resultant suspension may be filtered or the mixture may be extracted with a suitable water immiscible solvent such as dichloromethane and the organic layer is concentrated to obtain the compound of formula V.

The obtained crude compound may be purified using known purification techniques such as slurrying and recrystallization using a suitable solvent to get pure compound of formula V.

In a third aspect the present application provides use of compound of formula V or a salt thereof, prepared by the process described in the present application, in the preparation of Siponimod and its slats.

In a fourth aspect the present application provides a process for preparation of Siponimod of formula I, comprising:

a) reacting a compound of formula VI with a compound of formula VII in presence of a suitable base to get a compound of formula V

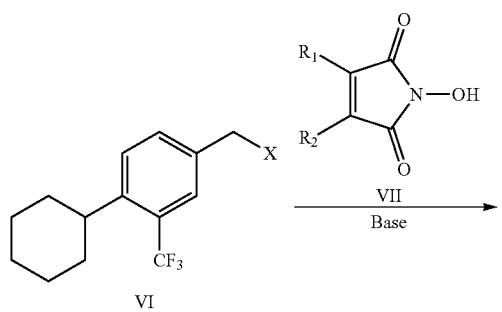

b) reacting the compound of formula V with a suitable amine to form a compound of formula IV

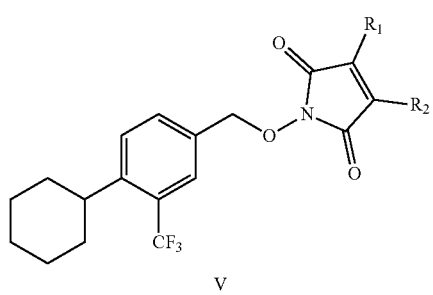

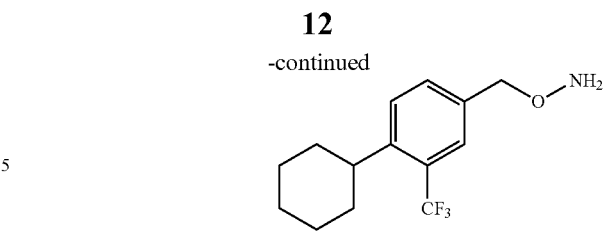

c) reacting the compound of formula IV with 1-(3-ethyl-4-(hydroxymethyl)phenyl)ethan-1-one of formula XII to form a compound of formula III

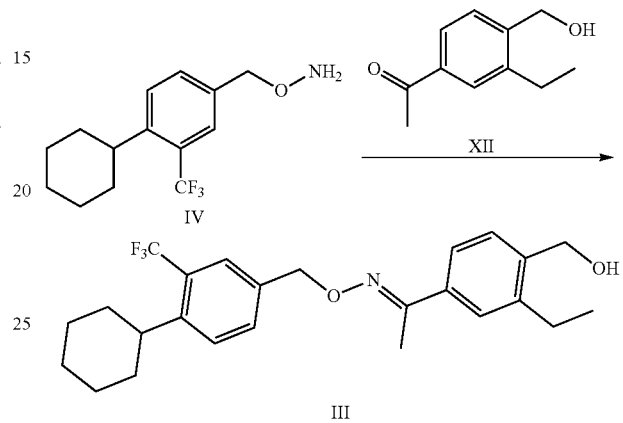

d) oxidizing the compound of formula III using a suitable oxidizing agent to form a compound of formula II

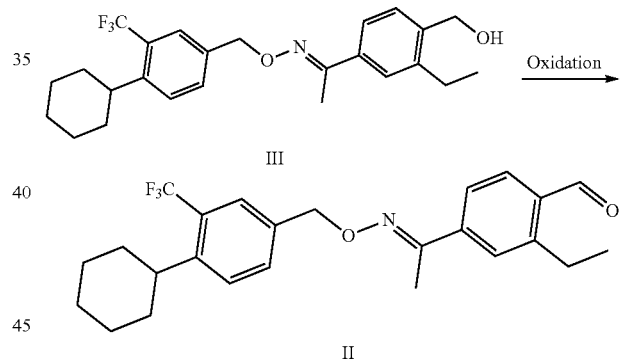

e) reacting the compound of formula II with azetidine-3-carboxylic acid to form Siponimod of formula I.

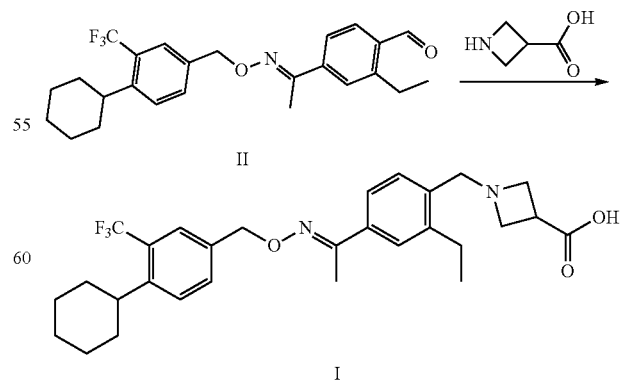

f) optionally, converting Siponimod into its pharmaceutically acceptable salt.

The step (a) of the process involves reaction of compound of formula VI with a compound of formula VII in presence of a suitable base such as triethylamine or diisopropyl ethylamine, and a suitable solvent such as N,N-dimethylformamide or N,N-dimethylacetamide. The compound of formula VI can be prepared by the process described in this application or any of the processes described in the art.

The compound of formula VI, the solvent, the base and he compound of formula VII are mixed and the resulted mixture may be stirred for about 10 minutes to about 10 hours at a temperature of about 30° C. to about 100° C.

After completion of the reaction the reaction mixture is added to water and the resultant suspension may be filtered or the mixture may be extracted with a suitable water immiscible solvent such as dichloromethane and the organic layer is concentrated to obtain the compound of formula V.

The obtained crude compound may be purified using known purification techniques such as slurrying and recrystallization using a suitable solvent to get pure compound of formula V.

The step (b) involves reaction of the compound of formula V with a suitable amine such as n-Butylamine, hydroxylamine and hydrazine in presence of a suitable solvent such as methanol, ethanol, isopropanol, acetone, THF and the like to form the compound of formula IV.

The compound of formula V, the solvent, and a suitable amine are mixed and the resulted mixture may be stirred for about 10 minutes to about 10 hours at a temperature of about 0° C. to about 50° C.

After completion of the reaction the reaction mixture may be concentrated and the resulted crude may be purified using a suitable acid such as hydrochloric acid.

The step (c) of the process involves reaction of compound of formula IV with a compound of formula XII in presence of aa suitable solvent such as methanol, ethanol, isopropanol, THF and the like. The compound of formula XII can be prepared by the process described in this application or any of the processes described in the art.

The compound of formula IV, the solvent, and the compound of formula XII are mixed and the resulted mixture may be stirred for about 10 minutes to about 20 hours at a temperature of about 30° C. to about 100° C.

After completion of the reaction the reaction mixture may be concentrated and the resulted crude compound of formula III may be purified using known purification techniques such as slurrying and/or recrystallization using a suitable solvent or using silica gel column chromatography.

The step (d) involves oxidation of the compound of formula III using a suitable oxidizing agent such as $MnO_2$, $CrO_3$, $K_2CrO_7$, $TiO_2$ and $KMnO_4$ and a suitable solvent such as heptane, n-hexane, toluene and the like to form a compound of formula II.

The compound of formula III, the solvent, and the oxidizing agent are mixed and the resulted mixture may be stirred for about 10 minutes to about 20 hours at a temperature of about 30° C. to about 120° C.

After completion of the reaction the reaction mixture may be filtered to remove the oxidizing agent and other inorganic materials and the filtrate may be concentrated and the resulted crude compound of formula II may be purified using known purification techniques such as slurrying and/or recrystallization using a suitable solvent or using silica gel column chromatography.

The step (e) involves reaction of compound of formula II with azetidine-3-carboxylic acid using a suitable solvent such as methanol, ethanol, isopropanol and a suitable acid such as acetic acid and a suitable reducing agent such as Sodium cyano borohydride to form Siponimod of formula I.

The compound of formula II, the solvent, azetidine-3-carboxylic acid, acetic acid and Sodium cyano borohydride are mixed and the resulted mixture may be stirred for about 10 minutes to about 5 hours at a temperature of about 0° C. to about 50° C.

After completion of the reaction the reaction mixture may be concentrated and the resulted crude is added to water and the mixture is extracted with a suitable solvent such as ethylacetate and the solvent layer may be concentrated to isolate the crude Siponimod of formula I. The crude Siponimod base may be purified using known purification techniques such as slurrying and/or recrystallization using a suitable solvent or using silica gel column chromatography.

The Siponimod base may be converted into a suitable acid addition salt such as Siponimod fumarate salt. The Siponimod base, a suitable solvent such as ethanol and fumaric acid are mixed and the resulted mixture may be stirred for about 10 minutes to about 3 hours at a temperature of about 0° C. to about 50° C. The resulted mass may be filtered and the filtrate may be concentrated to obtain crude Siponimod fumarate salt. The crude salt may be purified by slurrying in a suitable solvent such as acetonitrile and acetone.

In a fifth aspect the present application provides a process for preparation of compound of formula V-A, comprising:

a) reacting a compound of formula XI with cyclohexanone to form a compound of formula X

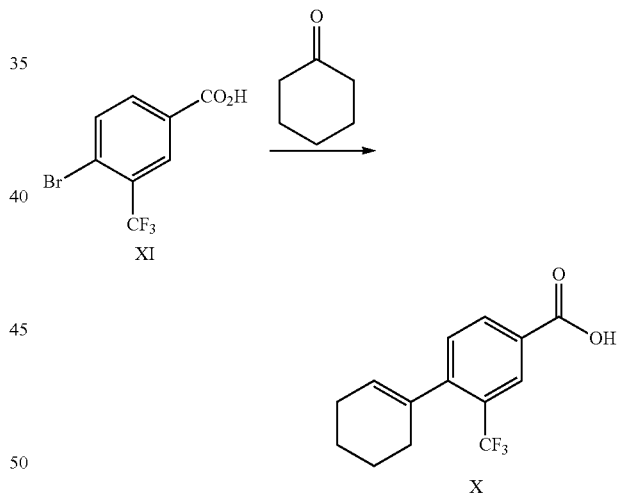

b) hydrogenating the compound of formula X in presence of suitable catalyst to form a compound of formula IX

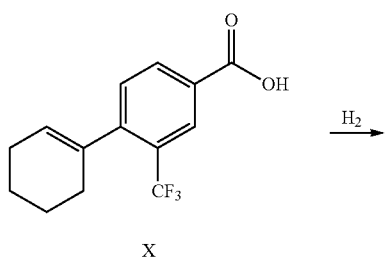

-continued

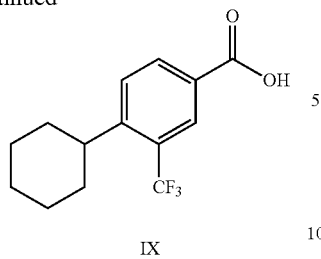

IX c) reducing the compound of formula IX using a suitable reducing agent to form a compound of formula VIII

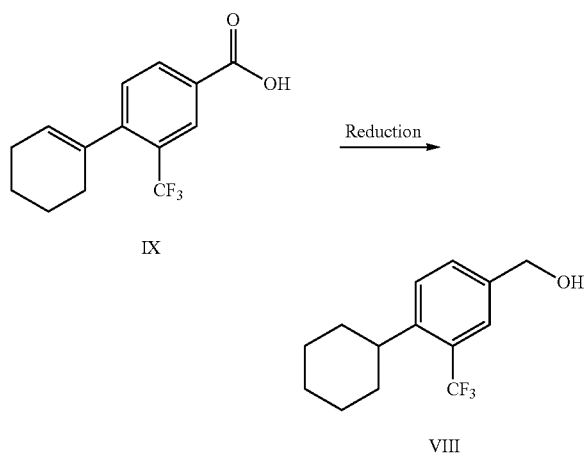

d) reacting the compound of formula VIII with a brominating agent to form a compound of VI-A

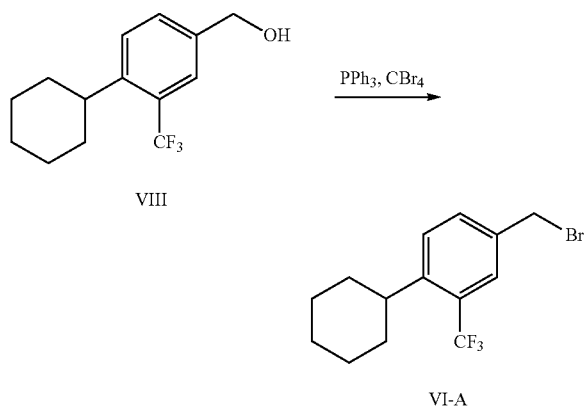

e) reacting a compound of formula VI-A with 2-hydroxyisoindoline-1,3-dione in presence of a suitable base to get a compound of formula V-A.

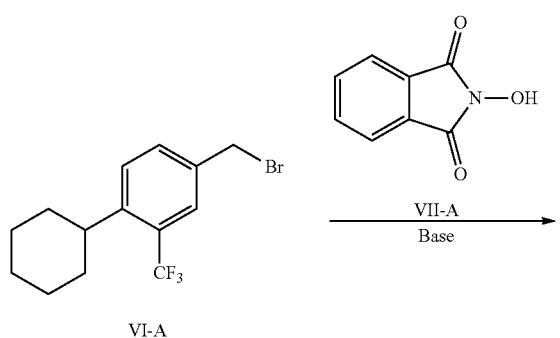

-continued

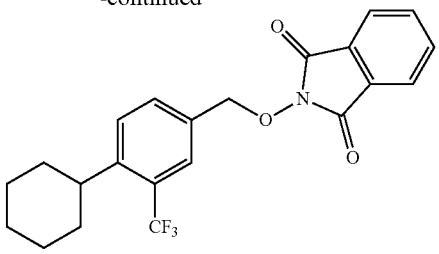

V-A

The step (a) of the process involves reaction of a compound of formula XI with cyclohexanone in presence of a suitable metal alkoxide such as sodium tert-butoxide or lithium tert-butoxide, a suitable catalyst such as tris-(dibenzylidene acetone)-dipalladium and X-Phos and a suitable solvent such as 1,4-dioxane to form a compound of formula X.

The compound of formula XI, Cyclohexanone, 1,4-dioxane and Tosyl hydrazide are mixed and the resulted mixture may be stirred for about 5 minutes to about 1 hour. Lithium tert.-butoxide, tris-(dibenzylidene acetone)-dipalladium and X-Phos are added to the reaction mixture and the resulted mixture may be stirred for about 30 minutes to about 20 hours at a temperature of about 30° C. to about 150° C.

After completion of the reaction the mixture may be filtered and the filtrate may be concentrated. The residue may be added to a suitable solvent such as ethylacetate and the solvent layer may be washed to remove the impurities. The solvent layer may be concentrated to get the compound of formula X.

The step (b) process involves hydrogenation of the compound of formula X using hydrogen gas and a suitable catalyst such Palladium or Nickel and a suitable solvent such as methanol to form a compound of formula IX.

The compound of formula X, solvent and the catalyst are mixed in an autoclave. To the vessel hydrogen gas is filled upto about 100 psi and resulting mixture is hydrogenated at about 1 hour to about 20 hours at a temperature of about 0° C. to about 50° C.

After completion of the reaction the mixture may be filtered and the filtrate containing the compound of formula IX may be concentrated or may be used directly in the next step.

The step (c) involves reduction of the compound of formula IX using a suitable reducing agent such as LiAlH$_4$ or NaBH$_4$ and a suitable solvent such as tetrahydrofuran to form a compound of formula VIII.

The compound of formula IX, solvent and the reducing agent are mixed and the resultant mixture is stirred for about 10 minutes to about 3 hours at a temperature of about 0° C. to about 50° C.

After completion of the reaction the mixture may be quenched with water and the resultant solution may be extracted with a suitable solvent such as ethylacetate. The solvent layer may be concentrated to get crude compound of formula VIII. The crude may be purified using known purification techniques such as slurrying and/or recrystallization using a suitable solvent or using silica gel column chromatography.

The step (d) involves bromination of the compound of formula VIII using a suitable brominating agent such as PBr$_3$ or POBr$_3$ and a suitable solvent such as dichloromethane to form a compound f formula VI-A.

The compound of formula VIII, solvent and the brominating agent are mixed and the resultant mixture is stirred for about 10 minutes to about 5 hours at a temperature of about 0° C. to about 30° C.

After completion of the reaction the mixture may be quenched with water and the resultant solution may be extracted with a suitable solvent such as dichloromethane. The solvent layer may be concentrated to get the compound of formula VI-A.

The step (e) process involves reaction of compound of formula VI-A with 2-hydroxyisoindoline-1,3-dione(compound of formula VII-A) in presence of a suitable base such as triethylamine or diisopropyl ethylamine, and a suitable solvent such as N,N-dimethylformamide or N,N-dimethylacetamide.

The compound of formula VI-A, the solvent, the base and the compound of formula VII-A are mixed and the resulted mixture may be stirred for about 10 minutes to about 10 hours at a temperature of about 30° C. to about 100° C.

After completion of the reaction the reaction mixture is added to water and the resultant suspension may be filtered or the mixture may be extracted with a suitable water immiscible solvent such as dichloromethane and the organic layer is concentrated to obtain the compound of formula V-A.

In another aspect the present application provides an alternate process for preparation of compound of formula VIII as shown below:

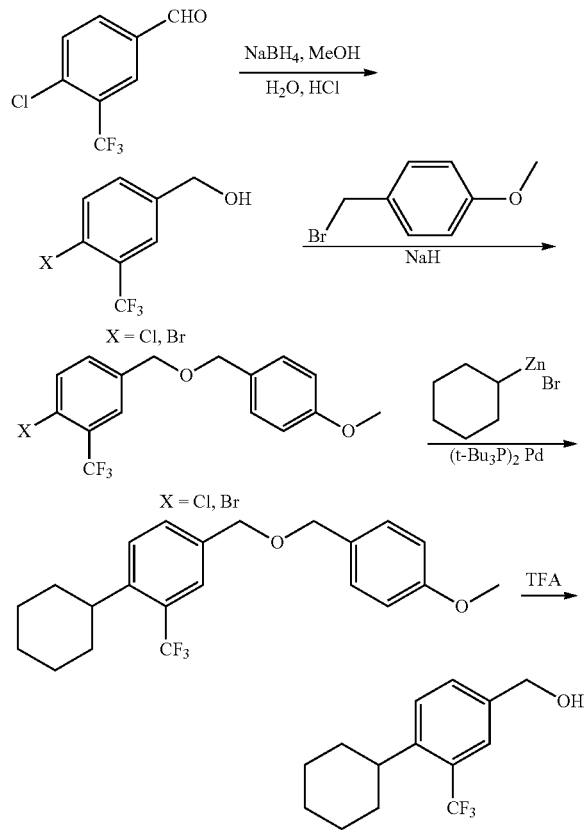

In another aspect the present application provides use of compound of formula V-A, prepared by the process described in the present application, in the preparation of Siponimod and its salts.

In another aspect the present application provides a process for preparation of Siponimod hemifumarate. The Siponimod base may be converted into a suitable acid addition salt such as Siponimod hemifumarate salt. The Siponimod base, a suitable solvent such as ethanol and fumaric acid are mixed and the resulted mixture may be stirred for about 10 minutes to about 3 hours at a temperature of about 0° C. to about 50° C. The resulted mass may be filtered and the filtrate may be concentrated to obtain crude Siponimod hemifumarate salt. The crude salt may be purified by slurrying in a suitable solvent such as acetonitrile or acetone.

In another aspect, the present application provides a pharmaceutical composition comprising Siponimod hemifumarate prepared by the process of the present invention and a pharmaceutically acceptable carrier.

In another aspect, the present application provides a crystalline Form SHF1 of Siponimod hemifumarate, characterized by a PXRD pattern comprising the peak at about 7.52±0.2° 2θ.

In another aspect, the present application provides a process for the preparation of crystalline Form SHF1 of Siponimod hemifumarate, comprising,
 (a) suspending Siponimod hemifumarate in water,
 (b) heating the suspension of step (a),
 (c) isolating the solid, and
 (d) drying the solid to obtain crystalline Form SHF1 of Siponimod hemifumarate.

The step (a) involves mixing of Siponimod hemifumarate with water. Any physical form of Siponimod hemifumarate may be used as starting material. In step (b) the suspension is heated to about 50° C. and the suspension may be stirred for about 10 minutes to about 10 hours. The step (c) involves isolation of crystalline Form SHF1 of Siponimod hemifumarate.

Isolation of the solid may be carried out by any methods known in the art or procedures described in the present application. In an embodiment, the solid may be isolated by filtration by gravity or suction. In step (d) the isolated solid is dried under vacuum at about 40° C. to about 80° C. to obtain crystalline Form SHF1 of Siponimod hemifumarate.

In another aspect, the crystalline Form SHF1 of Siponimod hemifumarate is further characterized by a PXRD pattern comprising the peaks at about 11.39, 12.51, 13.28, 14.31, 15.62, and 17.43±0.2° 2θ.

Figure 9:
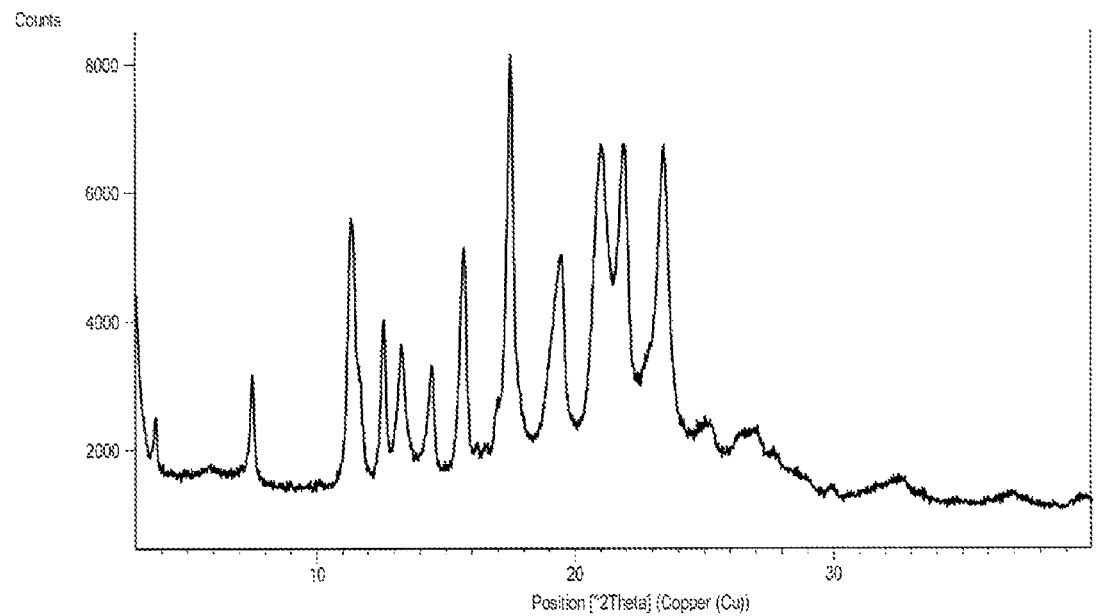
FIG. 9 is powder X-ray diffraction ("PXRD") pattern of crystalline form SHF1 of Siponimod hemifumarate prepared according to Example 19.

In another aspect, the crystalline Form SHF1 of Siponimod hemifumarate is characterized by the PXRD pattern of FIG. 9.

In another aspect, the present application provides a process for the preparation of crystalline Form SHF1 of Siponimod hemifumarate, characterized by a PXRD pattern comprising the peak at about 7.52±0.2° 2θ, comprising:
 (e) providing a mixture of Siponimod hemifumarate and water,
 (f) heating the mixture of step (a),
 (g) adding an organic solvent to the mixture, and
 (h) isolating and drying the solid to obtain crystalline Form SHF1 of Siponimod hemifumarate.

The step (a) involves mixing of Siponimod hemifumarate with water. Water may be 1:1 to 1:50 to the weight of Siponimod hemifumarate. Any physical form of Siponimod hemifumarate may be used as starting material. In step (b) the suspension is heated to about 40° C. to about 100° C. and the suspension may be stirred for about 10 minutes to about 10 hours. The step (c) involves addition of an organic solvent such as acetonitrile, acetone, THF, ethylacetate and the like to the hot mixture and the resulted mixture may be stirred for about 10 minutes to about 5 hours. The step (d) involves isolation of crystalline Form SHF1 of Siponimod hemifumarate.

Isolation of the solid may be carried out at about 0° C. to about 30° C. by any methods known in the art or procedures described in the present application. In an embodiment, the solid may be isolated by filtration by gravity or suction. The isolated solid is dried under vacuum at about 40° C. to about 80° C. to obtain crystalline Form SHF1 of Siponimod hemifumarate characterized by a PXRD pattern comprising the peak at about 7.52±0.2° 2θ.

In another aspect, the present application provides a crystalline Form SHF2 of Siponimod hemifumarate, characterized by a PXRD pattern comprising the peaks at about 5.38 and 8.13±0.2° 2θ.

In another aspect, the present application provides a process for the preparation of crystalline Form SHF2 of Siponimod hemifumarate, comprising,
  (a) providing a mixture of Siponimod hemifumarate and 1,4-dioxane,
  (b) stirring the mixture of step (a), and
  (c) isolating the crystalline Form SHF2 of Siponimod hemifumarate The step (a) involves mixing of Siponimod hemifumarate with 1,4-dioxane. Any physical form of Siponimod hemifumarate may be used for the preparation of the mixture. In step (b) the mixture is stirred for about 10 minutes to about 10 hours at a temperature 0° C. to about 50° C. The step (c) involves isolation of the crystalline Form SHF2 of Siponimod hemifumarate.

Isolation may be carried out by any methods known in the art or procedures described in the present application. In an embodiment, the solid may be isolated by filtration by gravity or suction. The isolated solid may be dried under vacuum at about 20° C. to about 40° C. to obtain crystalline Form SHF2 of Siponimod hemifumarate.

In another aspect, the crystalline Form SHF2 of Siponimod hemifumarate is further characterized by a PXRD pattern comprising the peaks at about 10.89, 13.67, 14.98, 16.45, 19.23, 20.65, 22.13 and 23.19±0.2° 2θ.

Figure 10:
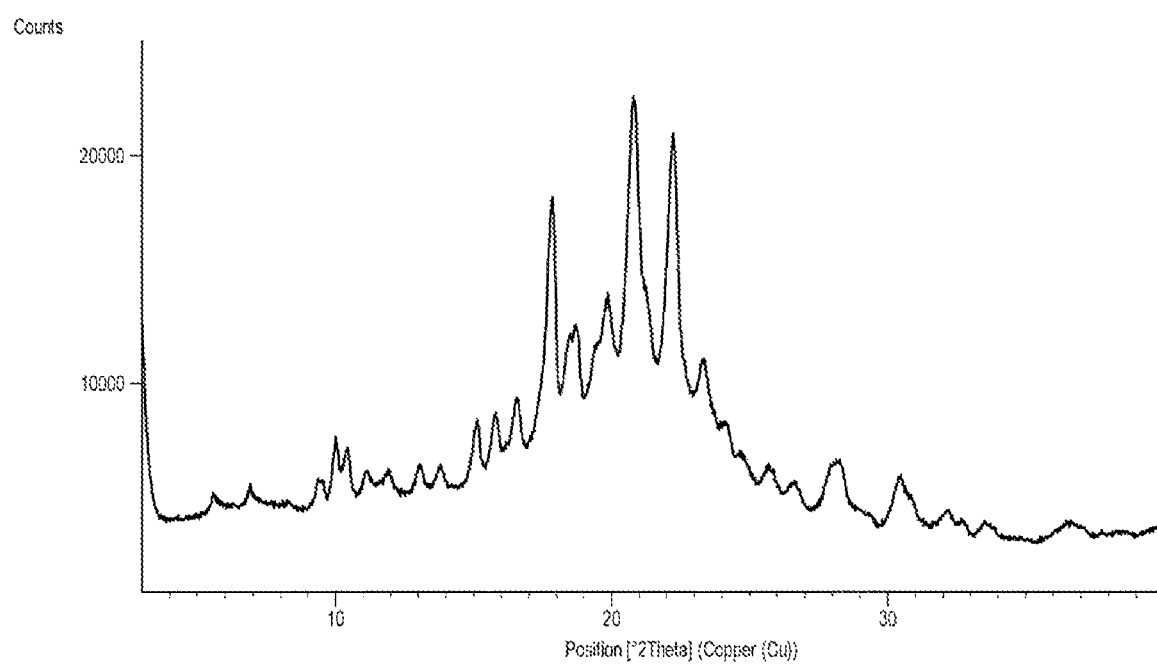
FIG. 10 is powder X-ray diffraction pattern of crystalline form SHF2 of Siponimod hemifumarate prepared according to Example 20.

In another aspect, the crystalline Form SHF2 of Siponimod hemifumarate is characterized by the PXRD pattern of FIG. 10.

In another aspect, the present application provides a crystalline Form SF1 of Siponimod monofumarate, characterized by a PXRD pattern comprising the peaks at about 11.62, 12.24, 13.52, and 16.7±0.2° 2θ.

In another aspect, the present application provides a process for the preparation of crystalline Form SF1 of Siponimod monofumarate, comprising,
  (a) providing a mixture of Siponimod base and an organic solvent,
  (b) adding fumaric acid to the mixture of step (a), and
  (c) isolating the crystalline Form SF1 of Siponimod monofumarate
  Providing a mixture in step (a) includes:
    (i) direct use of a reaction mixture containing Siponimod monofumarate that is obtained in the course of its synthesis; or
    (ii) direct use of reaction mixture containing Siponimod monofumarate that is obtained by treating Siponimod with fumaric acid; or
    (iii) dissolving Siponimod monofumarate in a solvent.

The step (a) involves mixing of Siponimod base with a suitable organic solvent such as 2-propanol, 1-butanol, 2-butanol and ethylformate. Any form of Siponimod base may be used for the preparation of the mixture. The step (b) involves addition of fumaric acid to the mixture of step (a). The fumaric acid may be added as solid or as a solution by dissolving in in any suitable solvent. Preferably the solvent is same as the solvent used in step (a).

The resulted mixture is stirred for about 10 minutes to about 10 hours at a temperature 0° C. to about 50° C. The step (c) involves isolation of the crystalline Form SF1 of Siponimod monofumarate.

Isolation may be carried out by any methods known in the art or procedures described in the present application. In an embodiment, the solid may be isolated by filtration by gravity or suction. The isolated solid may be dried under vacuum at about 30° C. to about 50° C. to obtain crystalline Form SF1 of Siponimod monofumarate.

In another aspect, the crystalline Form SF1 of Siponimod monofumarate is further characterized by a PXRD pattern comprising the peaks at about 7.0, 10.56, 13.52, 14.11, 17.82, and 21.35±0.2° 2θ.

Figure 11:
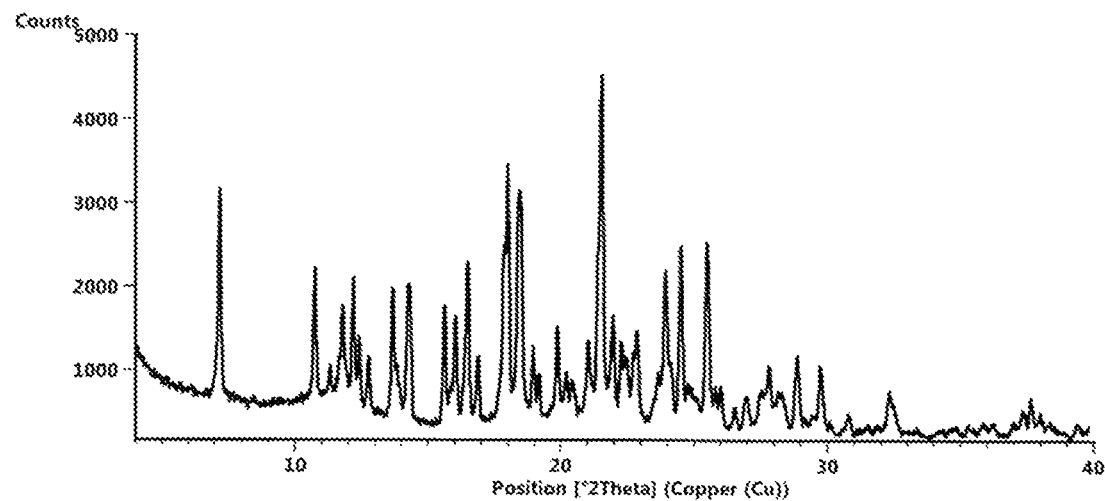
FIG. 11 is powder X-ray diffraction pattern of crystalline form SF1 of Siponimod monofumarate prepared according to Example 21.

In another aspect, the crystalline Form SF1 of Siponimod monofumarate is characterized by the PXRD pattern of FIG. 11.

In another aspect, the present application provides use of any of crystalline forms of Siponimod hemifumarate and Siponimod monofumarate of the present invention in the purification of Siponimod hemifumarate and in the preparation of other crystalline forms.

In another aspect, the present application provides pharmaceutical composition comprising any of crystalline forms of Siponimod hemifumarate and Siponimod monofumarate described in this application and one or more pharmaceutically acceptable excipients.

In a first aspect, the present application provides di-p-Toluolyl-L-tartaric acid salt of Siponimod. The di-p-Toluolyl-L-tartaric acid salt of Siponimod may exist in a crystalline form.

Figure 6:
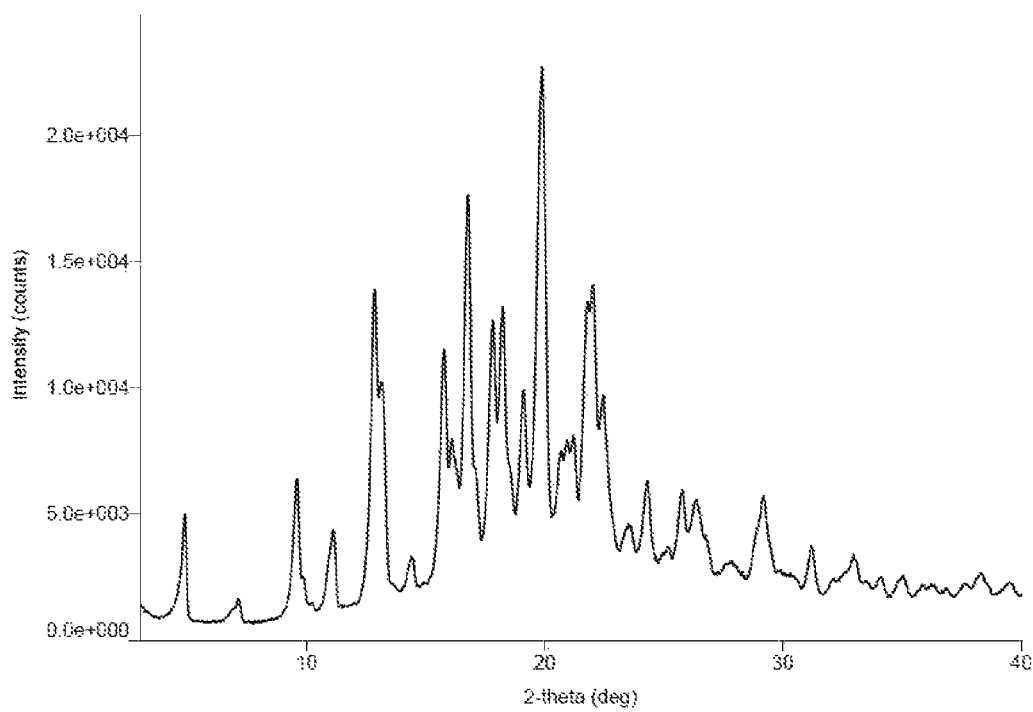
FIG. 6 is powder X-ray diffraction ("PXRD") pattern of Siponimod di-p-Toluolyl-L-tartrate prepared according to Example 16.

In a further aspect, the present application provides crystalline Form A of di-p-Toluolyl-L-tartaric acid salt of Siponimod. The crystalline Form A of di p-Toluolyl-L-tartaric acid salt of Siponimod is characterized in that it provides an X-ray powder diffraction pattern substantially as shown in FIG. 6.

In a further aspect, the present application provides crystalline Form A of di-p-Toluolyl-L-tartaric acid salt of Siponimod, wherein said crystalline Form A is characterized by X-ray powder diffraction pattern comprising the peaks at about 16.760, 17.800, 18.210 and 19.88°±0.2° 2θ.

In a further aspect, the present application provides di-benzoyl-D-tartaric acid salt of Siponimod. The di-benzoyl-D-tartaric acid salt of Siponimod may exist in a crystalline form.

Figure 7:
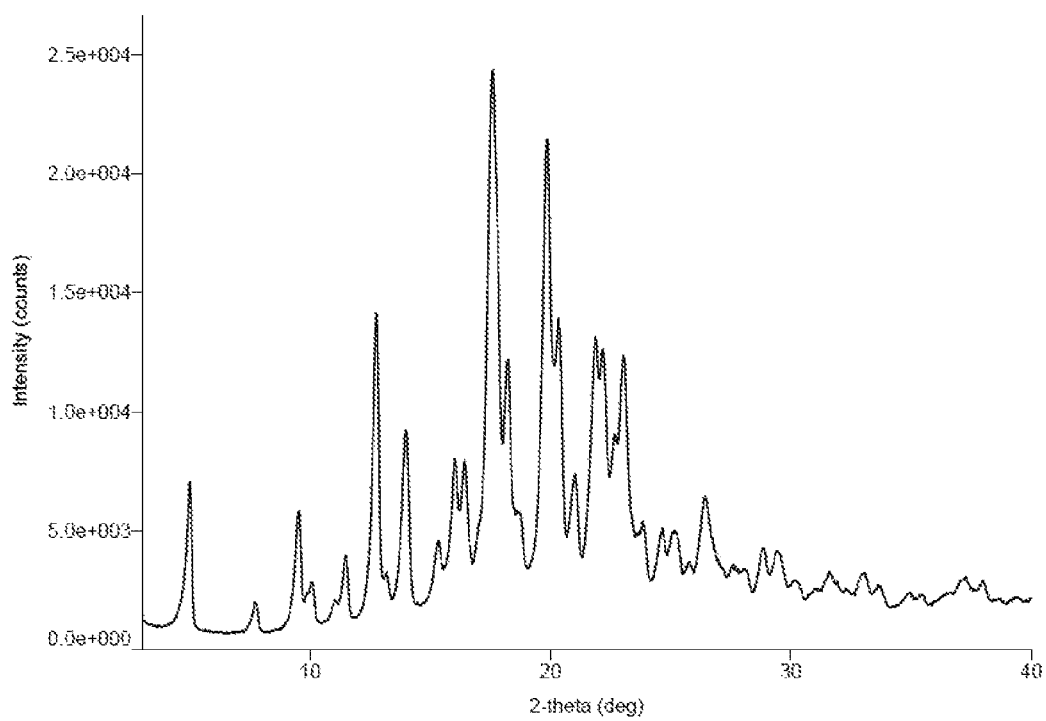
FIG. 7 is powder X-ray diffraction pattern of Siponimod di-benzoyl-D-tartrate prepared according to Example 17.

In a further aspect, the present application provides crystalline Form A of di-benzoyl-D-tartaric acid salt of Siponimod. The crystalline Form A of di-benzoyl-D-tartaric acid salt of Siponimod is characterized in that it provides an X-ray powder diffraction pattern substantially as shown in FIG. 7.

In a further aspect, the present application provides crystalline Form A of di-benzoyl-D-tartaric acid salt of Siponimod, wherein said crystalline Form A is characterized by X-ray powder diffraction pattern comprising the peaks at about 12.77°, 14.01°, 17.57°, 19.84° and 20.31°±0.2° 2θ.

In a further aspect, the present application provides isethionic acid salt of Siponimod. The isethionic acid salt of Siponimod may exist in a crystalline form.

In a further aspect, the present application provides crystalline Form A of isethionic acid salt of Siponimod. The crystalline Form A of isethionic acid salt of Siponimod is characterized in that it provides an X-ray powder diffraction pattern substantially as shown in FIG. 10.

In a further aspect, the present application provides crystalline Form A of isethionic acid salt of Siponimod, wherein said crystalline Form A is characterized by X-ray powder diffraction pattern comprising the peaks at about 13.32°, 16.33°, 16.75°, 17.84°, 20.06° and 22.30°±0.2° 2θ.

The crystalline forms of the salts of Siponimod described herein possess beneficial pharmaceutical properties that make them possible candidates for pharmaceutical development.

According to a further aspect of the application, there is provided a method of preparing a salt of Siponimod, including a crystalline form thereof, as defined herein, said method comprising the step of reacting the Siponimod free base with the corresponding acid in the presence of a suitable solvent or mixture of solvents.

In a specific aspect, the present application provides a method of preparing di-p-Toluolyl-L-tartaric acid salt of Siponimod, including crystalline Form A thereof, as defined herein, said method comprising the step of reacting Siponimod free base with di-p-Toluolyl-L-tartaric acid in the presence of a suitable solvent.

In a further aspect, the present application provides a method of preparing di-benzoyl-D-tartaric acid salt of Siponimod, including crystalline Form A thereof, as defined herein, said method comprising the step of reacting Siponimod free base with di-benzoyl-D-tartaric acid in the presence of a suitable solvent.

In a further aspect, the present application provides a method of preparing isethionic acid salt of Siponimod, including crystalline Form A thereof, as defined herein, said method comprising the step of reacting Siponimod free base with isethionic acid in the presence of a suitable solvent.

Any suitable solvent or mixture of solvents may be used to form the salts of Siponimod and their crystalline forms thereof defined herein.

A person skilled in the art will be able to select appropriate reaction times and conditions for carrying out the salt formation reaction.

Suitably, the Siponimod free base is dissolved together with the corresponding acid in a suitable solvent (such as those described in the accompanying examples). Alternatively, a solution of Siponimod free base may be dissolved in a suitable solvent and mixed with a solution of the corresponding acid (which is dissolved in either the same or a compatible solvent). Suitably, the solution is stirred to facilitate mixing of the Siponimod free base and the corresponding acid. The solution may be mixed at ambient temperature although the procedure may also be performed at higher temperatures.

The salts of Siponimod and their crystalline forms defined herein may be isolated by concentrating the reaction mixture and stirring the residue in a suitable solvent and isolating the salts by a known method such as filtration.

Alternatively, the salts of Siponimod and their crystalline forms defined herein may be isolated using techniques which are well known to those skilled in the art, for example decanting, filtering or centrifuging. Suitably, the salt is collected by filtration.

The method may additionally comprise the further step of washing the salt of Siponimod with a suitable solvent; and drying the salt. Preferably the washed salt is dried under vacuum.

The Siponimod salts of the present application can also be isolated as amorphous solids by known methods such as concentration of the reaction mixture, spray drying of the reaction mixture and lyophilization of the reaction mixture.

In a further aspect, the present application provides a pharmaceutical composition, comprising a salt of Siponimod or a crystalline form thereof, optionally with one or more pharmaceutically acceptable excipients.

In a further aspect, the present application provides the use of salts of Siponimod and crystalline forms thereof described herein for the preparation of Siponimod free base, other Siponimod salts and solid state forms thereof by converting the salt of Siponimod or a crystalline form of the present application into another salt of Siponimod or a solid state form thereof.

In a further aspect, the present application provides the use of salts of Siponimod and crystalline forms thereof described herein for the preparation of Siponimod hemifumarate by converting the salt of Siponimod or a crystalline form of the present application into Siponimod hemifumarate or a solid state form thereof.

In another aspect, the present application provides amorphous form of Siponimod hemifumarate.

In another aspect, the present application provides a process for preparing amorphous form of Siponimod hemifumarate which comprises;
 a) providing a solution of Siponimod hemifumarate in a solvent or a mixture solvents;
 b) removing solvent from the solution of Siponimod hemifumarate obtained in step a);
 c) recovering amorphous form of Siponimod hemifumarate.

Siponimod hemifumarate used as the input in the process for preparation of amorphous form of the present application can be prepared by any process known in the art or the process described in this application.

Providing a solution of Siponimod hemifumarate in step a) includes direct use of a reaction mixture containing Siponimod hemifumarate that is obtained in the course of its synthesis; or dissolving Siponimod hemifumarate in a solvent.

Any physical form of Siponimod hemifumarate may be utilized for providing the solution of Siponimod hemifumarate in step a).

Suitable solvents which can be used for dissolving Siponimod hemifumarate include but are not limited to: alcoholic solvents such as methanol, ethanol, isopropyl alcohol, n-propanol, isoamyl alcohol and the like; halogenated hydrocarbons such as dichloromethane, 1,2-dichloroethane, chloroform, carbon tetrachloride and the like; and any mixtures of two or more thereof.

After dissolution in step (a), the obtained solution may optionally be filtered to remove any insoluble particles. Suitable techniques to remove insoluble particles are filtration, centrifugation, decantation, and any other known techniques in the art. The solution can be filtered by passing through paper, glass fiber, or other membrane material, or a clarifying agent such as Celite. Depending upon the equipment used and the concentration and temperature of the solution, the filtration apparatus may need to be preheated to avoid premature precipitation of solid.

Step (b) involves removing solvent from the solution of Siponimod hemifumarate.

Suitable techniques which can be used for the removal of solvent include but not limited to evaporation, flash evaporation, simple evaporation, rotational drying, spray drying, agitated thin-film drying, Rotary vacuum paddle dryer, agitated nutsche filter drying, pressure nutsche filter drying, freeze-drying or any other suitable technique known in the art. The drying may be carried at normal pressure or under reduced pressure.

Step (c) involves recovering an amorphous form of Siponimod hemifumarate. The said recovery can be done by using the processes known in the art.

In an embodiment, the isolation of amorphous form of Siponimod hemifumarate may be carried out by employing any of the techniques known to a person skilled in art. Techniques for the isolation of amorphous form of Siponimod hemifumarate include, but not limited to: decantation, filtration by gravity or suction, centrifugation, and the like, and optionally washing with a solvent.

The resulting compound in step (c) may optionally be further dried. Drying can be carried out in a tray dryer, vacuum oven, air oven, cone vacuum dryer, rotary vacuum dryer, fluidized bed dryer, spin flash dryer, flash dryer, or the like. The drying can be carried out at temperatures of less than about 100° C., less than about 60° C., less than about 40° C., or any other suitable temperatures; at atmospheric pressure or under a reduced pressure; as long as the Siponimod hemifumarate is not degraded in its quality. The drying can be carried out for any desired times until the required product quality is achieved. Suitable time for drying can vary from few minutes to several hours for example from about 30 minutes to about 24 or more hours.

In another aspect, the present application provides amorphous form of Siponimod hemifumarate characterized by powder X-ray diffraction (PXRD) substantially as illustrated in FIG. 1.

In another aspect, the present application provides pharmaceutical composition comprising amorphous Siponimod hemifumarate and one or more pharmaceutically acceptable excipients.

In another aspect, the present application provides pharmaceutical composition comprising Siponimod or its pharmaceutically acceptable salt thereof prepared by the processes described in the present application and one or more pharmaceutically acceptable excipients.

In another aspect, the present application provides a solid dispersion comprising Siponimod hemifumarate and one or more pharmaceutically acceptable carrier.

In another aspect, the present application provides a process for preparing an amorphous solid dispersion comprising siponimod hemifumarate and one or more pharmaceutically acceptable carriers, the process comprising;
a) providing a solution comprising Siponimod hemifumarate and one or more pharmaceutically acceptable excipients,
b) removing solvent from the solution obtained in step (a), and
c) recovering an amorphous solid dispersion comprising Siponimod hemifumarate and one or more pharmaceutically acceptable excipient.

Providing a solution in step (a) includes direct use of a reaction mixture containing Siponimod hemifumarate that is obtained in the course of its synthesis or dissolving Siponimod hemifumarate and pharmaceutically acceptable carrier in a solvent or a mixture of solvents.

Any physical form of Siponimod hemifumarate may be utilized for providing the solution of step (a).

Suitable pharmaceutically acceptable carriers which can be used in step (a) include, but are not limited to: diluents such as starches, pregelatinized starches, lactose, powdered celluloses, microcrystalline celluloses, dicalcium phosphate, tricalcium phosphate, Polyethylene glycol, Copovidone, Soluplus, Silicified microcrystalline cellulose mannitol, sorbitol, sugar and the like; binders such as acacia, guar gum, tragacanth, gelatin, polyvinylpyrrolidones, hydroxypropyl celluloses, hydroxypropyl methylcelluloses such as HPMC-Phthalate, HPMC-AS, HPMC-15 CPS; pregelatinized starches and the like; disintegrants such as starches, sodium starch glycolate, pregelatinized starches, crospovidones, croscarmellose sodium, colloidal silicon dioxide and the like; lubricants such as stearic acid, magnesium stearate, zinc stearate and the like; glidants such as colloidal silicon dioxide and the like; solubility or wetting enhancers such as anionic or cationic or neutral surfactants; complex forming agents such as various grades of cyclodextrins and resins; release rate controlling agents such as hydroxypropyl celluloses, hydroxymethyl celluloses, hydroxypropyl methylcelluloses, ethylcelluloses, methylcelluloses, various grades of methyl methacrylates, waxes and the like. Other pharmaceutically acceptable excipients that are of use include but are not limited to film formers, plasticizers, colorants, flavoring agents, sweeteners, viscosity enhancers, preservatives, antioxidants, and the like.

In a preferred embodiment, the pharmaceutically acceptable carriers are PVP-K30, hydroxypropyl methylcellulose (HPMC), Kollidon VA64, Klucel LF, hydroxypropyl cellulose (HPC L) and Soluplus.

Suitable solvent that can be used for dissolving the Siponimod hemifumarate include but are not limited to: alcohol solvents such as methanol, ethanol, isopropyl alcohol, n-propanol, 2-butanol and the like; halogenated hydrocarbons such as dichloromethane, 1,2-dichloroethane, and the like; ketones such as acetone, ethyl methyl ketone, methyl isobutyl ketone and the like; esters such as ethyl acetate, n-propyl acetate, n-butyl acetate, t-butyl acetate and the like; ethers such as diethyl ether, dimethyl ether, di-isopropyl ether, 1,4-dioxane and the like; hydrocarbons such as toluene, xylene and the like; nitriles such as acetonitrile, propionitrile and the like; dimethylformamide, dimethylacetamide and dimethylsulfoxide, and any mixtures of two or more thereof.

In a specific aspect the solvent used in step (a) is selected form the group comprising methanol, ethanol, IPA and dichloromethane.

After dissolution in step (a), optionally undissolved particles, if any, may be removed suitably by filtration, centrifugation, decantation, and any other known techniques. The solution can be filtered by passing through paper, glass fiber, or other membrane material, or a clarifying agent such as celite. Depending upon the equipment used and the concentration and temperature of the solution, the filtration apparatus may need to be preheated to avoid premature crystallization.

Step (b) involves removing solvent from the solution obtained in step (a);

Suitable techniques which can be used for the removal of solvent include but not limited to evaporation, flash evaporation, simple evaporation, rotational drying such as drying using a rotavapor, spray drying, agitated thin-film drying, agitated nutsche filter drying, pressure nutsche filter drying, freeze-drying, filtration or any other technique known in the art.

Step (c) involves recovering an amorphous solid dispersion comprising Siponimod hemifumarate and one or more pharmaceutically acceptable carriers. The said recovery can be achieved by using the processes known in the art.

The resulting compound obtained in step (c) may optionally be further dried. Drying can be carried out in a tray dryer, vacuum oven, air oven, cone vacuum dryer, rotary vacuum dryer, fluidized bed dryer, spin flash dryer, flash dryer, or the like. The drying can be carried out at temperatures of less than about 75° C., less than about 50° C., or any other suitable temperatures; at atmospheric pressure or under a reduced pressure; as long as the Siponimod hemifumarate is not degraded in its quality. The drying can be carried out for any desired time until the required product quality is achieved. Suitable time for drying can vary from few minutes to several hours for example from about 30 minutes to about 24 or more hours.

Alternatively the amorphous solid dispersion of Siponimod hemifumarate can be prepared by mixing Siponimod hemifumarate with a suitable pharmaceutically acceptable carrier such as Syloid, PVP-K30, hydroxypropyl methylcellulose (HPMC), optionally in presence of a suitable solvent, followed by isolating and drying the amorphous solid dispersion of Siponimod hemifumarate.

When the active ingredient is hygroscopic or the formulation contains a hygroscopic ingredient, and to increase the stability of the amorphous form or a solid dispersion comprising Siponimod hemifumarate, addition of other carriers such as syloid, methyl cellulose, colloidal silicon dioxide, Eudragit, amorphous silica, micro crystalline cellulose, and the like, in the formulation has been found to be of particular value. Therefore these ingredients may be combined during the preparation of solid dispersion or after the preparation of amorphous Siponimod hemifumarate or solid dispersion to control hygroscopicity and to improve stability.

In another aspect, the present application provides pharmaceutical composition comprising amorphous Siponimod hemifumarate and one or more pharmaceutically acceptable excipients.

In another aspect, the present application provides a pharmaceutical composition comprising any one of Siponimod hemifumarate solid dispersion of the present invention and a pharmaceutically acceptable carrier.

In another aspect, the present application provides Siponimod hemifumarate having particle sizes less than about 300 μm, or less than about 100 μm, or less than about 50 μm, or less than about 20 μnm, or less than about 10 μm.

The present application provides Siponimod hemifumarate having a particle size distribution wherein the $10^{th}$ volume percentile particle size ($D_{10}$) is less than about 15 μm, the $50^{th}$ volume percentile particle size ($D_{50}$) is less than about 35 μm, and/or the $90^{th}$ volume percentile particle size ($D_{90}$) is less than about 60 μm.

The "$10^{th}$ volume percentile" as used herein, unless otherwise defined refers to the size of particles, below which 10% of the measured particle volume lies; "$50^{th}$ volume percentile" as used herein, unless otherwise defined refers to the size of particles, below which 50% of the measured particle volume lies, and "$90^{th}$ volume percentile" as used herein, unless otherwise defined refers to the size of particles, below which 90% of the measured particle volume lies.

Particle size distributions of Siponimod hemifumarate particles may be measured by any technique known in the art. For example, particle size distributions of Siponimod hemifumarate particles may be measured using light scattering equipment, such as, for example, a Malvern Master Sizer 2000 from Malvern Instruments Limited, Malvern, Worcestershire, United Kingdom (helium neon laser source, Siponimod hemifumarate suspended in light liquid paraffin, size range: 0.01 μm to 3000 μm).

In another aspect, the present application provides a method of treating multiple sclerosis comprising administering a pharmaceutical composition comprising Siponimnod or salts of siponimod or polymorphic forms thereof prepared by the processes of the present application and one or more pharmaceutically acceptable excipient.

Certain specific aspects and embodiments of the present application will be explained in greater detail with reference to the following examples, which are provided only for purposes of illustration and should not be construed as limiting the scope of the application in any manner. Variations of the described procedures, as will be apparent to those skilled in the art, are intended to be within the scope of the present application.

DEFINITIONS

The following definitions are used in connection with the present application unless the context indicates otherwise.

The term "about" when used in the present application preceding a number and referring to it, is meant to designate any value which lies within the range of ±10%, preferably within a range of ±5%, more preferably within a range of ±2%, still more preferably within a range of 1% of its value. For example "about 10" should be construed as meaning within the range of 9 to 11, preferably within the range of 9.5 to 10.5, more preferably within the range of 9.8 to 10.2, and still more preferably within the range of 9.9 to 10.1.

All percentages and ratios used herein are by weight of the total composition and all measurements made are at about 25° C. and about atmospheric pressure, unless otherwise designated. All temperatures are in degrees Celsius unless specified otherwise. As used herein, "comprising" means the elements recited, or their equivalents in structure or function, plus any other element or elements which are not recited. The terms "having" and "including" are also to be construed as open ended. All ranges recited herein include the endpoints, including those that recite a range "between" two values. Whether so indicated or not, all values recited herein are approximate as defined by the circumstances, including the degree of expected experimental error, technique error, and instrument error for a given technique used to measure a value.

Certain specific aspects and embodiments of the present application will be explained in greater detail with reference to the following examples, which are provided only for purposes of illustration and should not be construed as limiting the scope of the application in any manner. Reasonable variations of the described procedures are intended to be within the scope of the present invention. While particular aspects of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

EXAMPLES

Example-1: Preparation of 2-(trifluoromethyl)-2',3', 4',5'-tetrahydro-[1,1'-biphenyl]-4-Carboxylic Acid (Compound of Formula X)

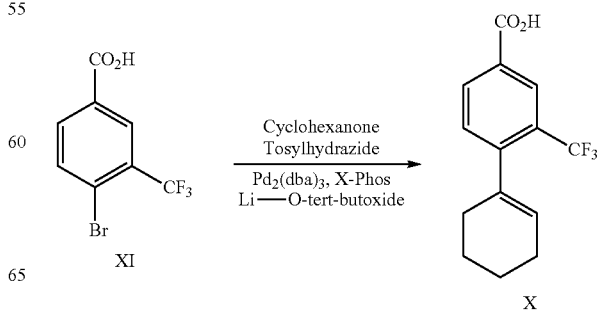

4-Bromo-3-(trifluoro methyl) benzoic acid (XI, 5.0 g), Cyclohexanone (3.85 mL), 1,4-dioxane (250 mL) and Tosyl hydrazide (6.92 g) were charged into a 1000 mL round bottom flask. The resulting reaction mixture was stirred for 10 min and degassed with nitrogen gas for 5 min. To the reaction mixture lithium tert.-butoxide (3.71 g), tris-(dibenzylidene acetone)-dipalladium (0) (Pd$_2$(dba)$_3$, 0.255 g) and X-Phos (0.531) added in one portion and the resulted mixture was degassed with nitrogen gas for 5 min. The reaction mixture was stirred at 110° C. for 16 hours. The reaction mixture was cooled to 30° C. and 1N hydrochloric acid (10 mL) was added. The reaction mixture was filtered through celite pad and bed was washed with ethylacetate (20 mL). The filtrate was concentrated under reduced pressure at 45° C. and ethylacetate (100 mL) was added to the resultant residue. The organic layer was washed with 1N hydrochloric acid (10 mL) 10% NaCl solution (10 mL). The organic layer was dried over sodium sulphate and concentrated under reduced pressure at 45° C. The crude was purified with silica gel (60-120 mesh) column chromatography and compound was eluted in 10-15% EtOAc in Hexane. The organic layer was concentrated to yield 3.5 g of the compound of formula X as pale yellow solid. Purity: 81.69%.

Example-2: Preparation of 4-cyclohexyl-3-(trifluoromethyl)benzoic acid (Compound of Formula IX)

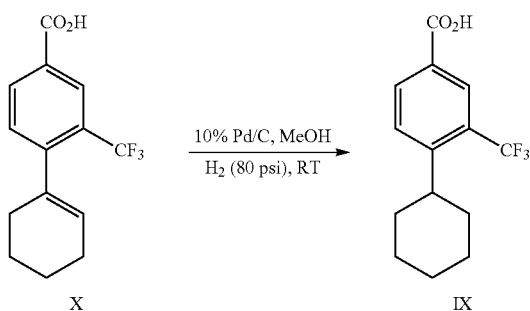

Compound of formula X (1.0 g) and methanol (10 mL) were charged into a 250 mL hydrogenation vessel and added 10% palladium on carbon at 28° C. Applied H$_2$-gas to the reaction mixture and evacuated the H$_2$-gas from the vessel. The vessel was filled with hydrogen gas and maintained 80 Psi at 29° C. for 72 hours. The reaction mixture was filtered through celite pad and the pad was washed with methanol (10 mL). The filtrate was concentrated under reduced pressure at 45° C. The crude compound of formula IX (0.87 g of pale yellow solid; HPLC purity: 93.23%) is used in the next step without any purification.

Example-3: Preparation of (4-cyclohexyl-3-(trifluoromethyl)phenyl)methanol (Compound of Formula VIII)

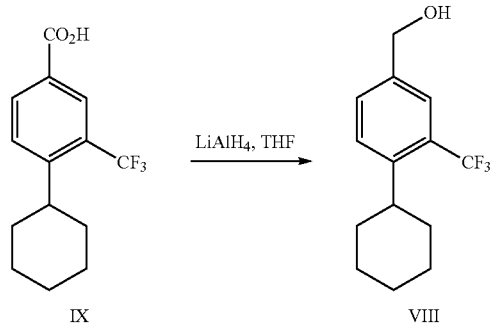

Compound of formula IX (0.87 g) and THF (50 mL) were charged into a 250 mL round bottom flask under N$_2$-atmosphere. The mixture was cooled to 0° C. and Lithium Aluminum hydride solution (2M in THF, 1.6 mL) was added drop wise to the reaction mixture. The resulting reaction mixture was stirred at 20° C. for 1 hour. The reaction mixture was cooled to 0° C. and quenched with cold water (1 mL) followed by 1N HCl (1 mL). The reaction mixture was diluted with ethylacetate (10 mL) and filtered through celite pad and the celite pad was washed with ethylacetate (5 mL). The organic layer was washed with brine solution (5 mL) and dried over sodium sulphate. The organic layer was concentrated under reduced pressure at 45° C. The crude was purified by silica gel (60-120 mesh) column chromatography and compound was eluted in 15% EtOAc in Hexane. The fractions containing the compound of formula VIII were combined and concentrated under reduced pressure at 45° C. to yield 603 mg of compound of formula VIII as colorless oil. HPLC purity: 97.64%.

Example-4: Preparation of 4-(bromomethyl)-1-cyclohexyl-2-(trifluoromethyl)benzene (Compound of Formula VI-A)

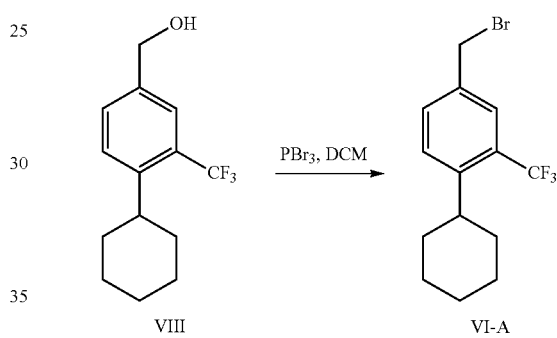

Compound of formula VIII (0.60 g) and DCM (6 mL) were charged into a 50 mL round bottom flask under N$_2$-atmosphere. The mixture was cooled to 0° C. and Phosphorous tribromide solution (1.0 M in DCM, 2.55 mL) was added drop wise to the reaction mixture. The resulting reaction mixture was stirred at 20° C. for 3 hours. The reaction mixture was quenched with cold saturated sodium bicarbonate solution (2.0 mL). Layers separated and the aqueous layer was extracted with DCM (10 mL). The organic layers were combined and washed with brine solution (5 mL) and dried over anhydrous sodium sulfate. The organic layer was concentrated under reduced pressure at 45° C. to yield 688 mg of compound of formula VI-A as colorless oil. HPLC purity: 99.92%.

Example-5: Preparation of 2-((4-cyclohexyl-3-(trifluoromethyl)benzyl)oxy)isoindoline-1,3-dione (Compound of Formula V-A)

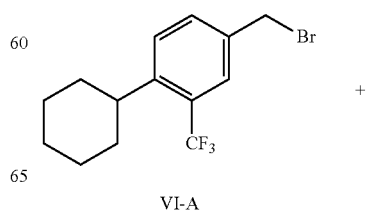

+

-continued

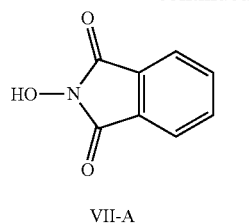

VII-A

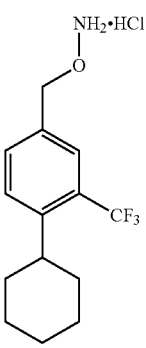

V-A

Compound of formula VI-A (0.65 g), N-hydroxy Phthalimide (VII-A, 0.495 g) and DMF (6.5 mL) were charged into a 25 mL round bottom flask under $N_2$-atmosphere. DIPEA (1.05 mL) was added to the mixture and the resultant mixture was heated to 70° C. and stirred for 1 hour. The reaction mixture was cooled to 28° C. and water (20 mL) was added to the mixture and stirred for 10 minutes. The precipitation was filtered and the solid was dried under vacuum to get 752 mg of compound of formula V-A as pale yellow solid. Purity: 99.70%.

Example-6: Preparation of (E)-1-(3-ethyl-4-(hydroxymethyl)phenyl)ethan-1-one-O-(4-cyclohexyl-3-(trifluoromethyl)benzyl)-oxime (Compound of Formula III)

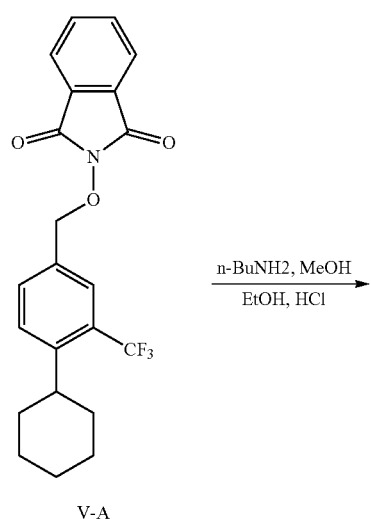

V-A

-continued

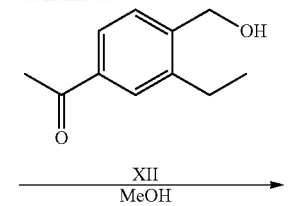

IV

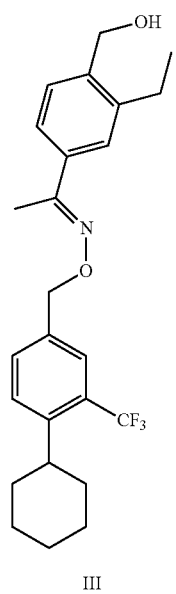

III

Compound of formula V-A (0.70 g) and Methanol (7 mL) were charged into a 25 mL round bottom flask under $N_2$-atmosphere and n-Butylamine (0.173 mL) was added drop-wise and the mixture was stirred at 29° C. for 1 hour. The reaction mixture was cooled to 0° C. and ethanolic HCl (4.0 mL) was added and stirred at 29° C. for 30 minutes. The reaction mixture was concentrated under reduced pressure at 45° C. The resulting crude compound was washed with MTBE (10 mL), filtered and the solid was dried under vacuum to yield compound of formula IV (HCl salt).

The compound of formula IV (HCl salt) was dissolved in methanol and a compound of formula XII (0.163 g) was added and the mixture was stirred for 16 hours at 28° C. The reaction mixture was concentrated under vacuum. The residue was purified by silica column chromatography and the compound was eluted in 15% EtOAc in Hexane. The fractions containing the compound of formula III were combined and concentrated under reduced pressure at 45° C. to yield 210 mg of the title compound as colorless oil. Purity: 94.54%.

Example-7: Preparation of (E)-4-(1-(4-cyclohexyl-3-(trifluoromethyl)benzyl)oxy)imino)ethyl)-2-ethyl-benzaldehyde (Compound of Formula II)

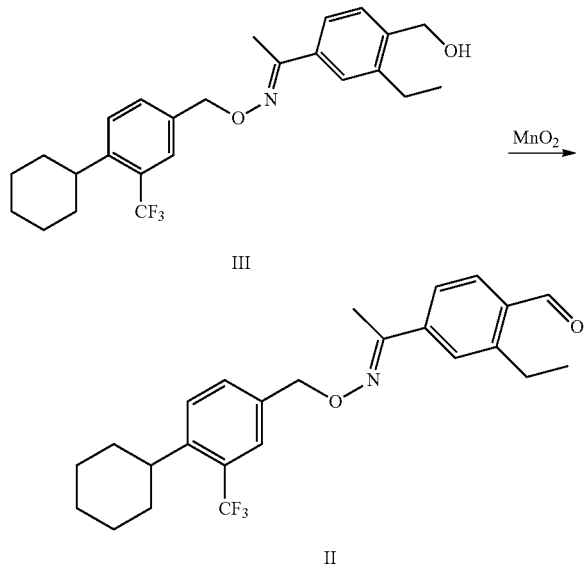

Compound of formula III (0.20 g) and heptane (8 mL) were charged into a 25 mL round bottom flask under N₂-atmosphere. Activated Manganese (IV) oxide (0.268 g) was added to the mixture and the resulted mixture was stirred for 3 hours at 60° C. The reaction mixture was filtered through a celite bed and the celite bed was washed with heptane. The filtrate was concentrated under vacuum at 45° C. to yield 0.18 g of the compound of formula II as off-white solid. Purity: 96.80%.

Example-8: Preparation of Siponimod (Compound of Formula I)

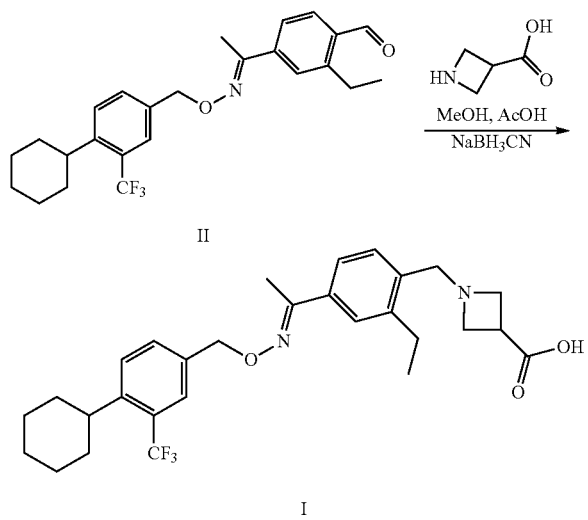

Compound of formula II (0.15 g) and methanol (3 mL) were charged into a 25 mL round bottom flask under N₂-atmosphere. 3-azetidine carboxylic acid (0.070 g) and acetic acid (0.18 mL) were added at 29° C. and the mixture was stirred for 30 minutes. Sodium Cyano borohydride (0.011 g) was dissolved in methanol (1.5 mL) and added to the reaction mixture at 25° C. and the reaction mixture was stirred for 1 hour at 28° C. Methanol was distilled-off from the reaction mixture under vacuum at 45° C. Water (10 mL) was added to the crude and extracted with ethylacetate (2×10 mL). The ethylacetate layer was washed with water (10 mL) and brine solution (10 mL). The organic layer was dried over anhydrous sodium sulfate and concentrated under reduced pressure at 45° C. The residue was purified by silica gel (100-200 mesh) column chromatography and compound was eluded in 8-10% MeOH in DCM. The fractions containing Siponimod concentrated under vacuum at 45° C. to yield 86 mg of Siponimod. Purity: 98.84%.

Example-9: Preparation of Siponimod Hemifumarate

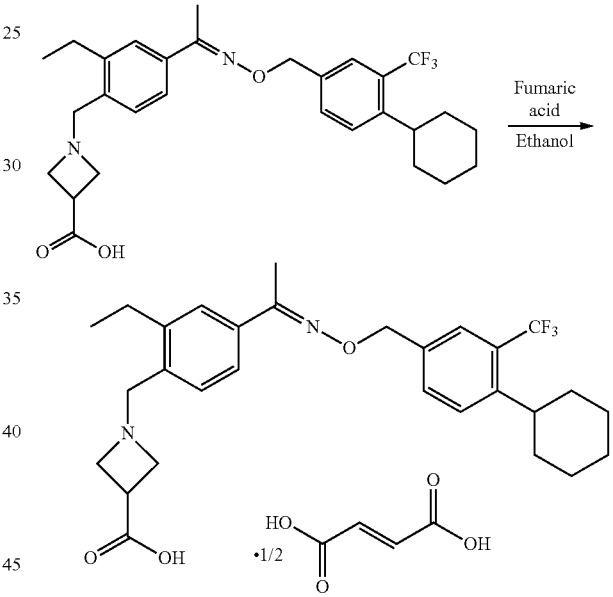

Siponimod base (144 g) and ethanol (1440 mL) were charged into a 2 L round bottom flask at 28° C. The mixture was heated to 40° C. and fumaric acid (12.95 g) was added and the mixture was for 30 minutes. The mixture was filtered through a celite bed and the bed was washed with ethanol (360 mL). The filtrate was concentrated under reduced pressure at 45° C. To the crude material acetonitrile (1100 mL) was added and stirred for 6 hours at 28° C. The precipitation was filtered and the solid was washed with acetonitrile (288 mL). The wet compound was dried in hot air oven at 35° C. for 4 hours to yield 110 g of crude Siponimod hemifumarate. The crude compound and acetone (1100 mL) were charged into a 2 L round bottom flask and the mixture was stirred at 56° C. for 30 minutes. The mixture was cooled to 29° C. and stirred for another 1 hour at 28° C. The precipitation was filtered and washed with acetone in a hot air oven at 40° C. to provide 90.5 g of Siponimod hemifumarate as off-white solid. Purity: 99.32%.

Example-10: Preparation of Amorphous Siponimod Hemifumarate

Siponimod hemifumarate (1.0 g) and a mixture of methanol and DCM (40 mL; 4 mL of methanol in 36 mL of DCM) were charged into a 100 mL round bottom flask under $N_2$-atmosphere. The mixture was stirred for 30 minutes at 28° C. The clear solution was filtered through a celite bed and the bed was washed with a mixture of methanol and DCM (10 mL; 1 mL of methanol in 9 mL of DCM). The filtrate was concentrated under vacuum at 45° C. to yield 0.9 g of amorphous Siponimod hemifumarate. Purity: 98.57%. PXRD as shown in FIG. 1.

Example-11: Preparation of 1-(3-ethyl-4-(hydroxymethyl)phenyl)ethan-1-one (Compound of Formula XII)

Example-11(a): Preparation of 1-(3-bromo-4-(hydroxymethyl)phenyl)ethan-1-one

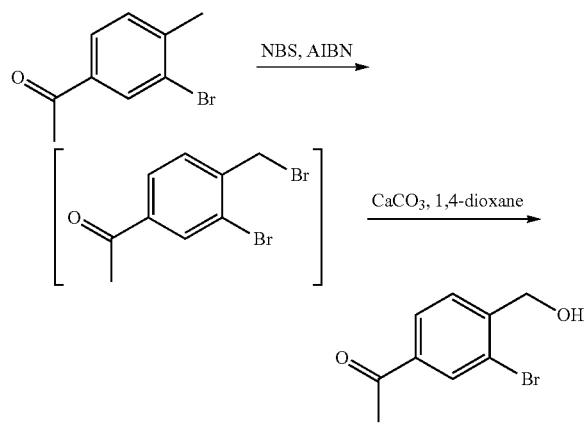

3-bromo-4-methyl-acetophenone (200 g), N-bromo succinimide (167 g), azo-bis-isobutyronitrile (30.8 g) and 1,2-dichloro ethane (2 L) were charged in a 3 L RBF equipped with reflux condenser and guard tube at 28° C. The reaction mixture was heated to 80° C. and stirred for 16 hours. The reaction was cooled to 30° C. and filtered through a celite bed and the celite bed was washed with DCM (200 mL). The filtrate was concentrated under reduced pressure at 50° C. To the crude 1,4-dioxane (1400 mL), water (1400 mL) and calcium carbonate (281.59 g) were charged and the reaction mixture was stirred for 16 hours at 100° C. The reaction mixture was cooled to 29° C. and filtered through a celite bed and the celite bed was washed with ethylacetate (500 mL). The filtrate was extracted with ethylacetate (3×500 mL). The organic layers were combined and washed with water (300 mL) and brine (300 mL). The organic layer was dried over sodium sulfate and concentrated under vacuum at 45° C. The crude compound was purified using silica gel chromatography and the compound was eluted in 15-25% EtOAc/Hexane. The fractions containing the compound were combined and concentrated under reduced pressure at 45° C. to yield 126.2 g of the title compound as off-white solid. Purity: 98.32%.

Example-11(b): Preparation of 1-(4-(hydroxymethyl)-3-vinylphenyl)ethan-1-one

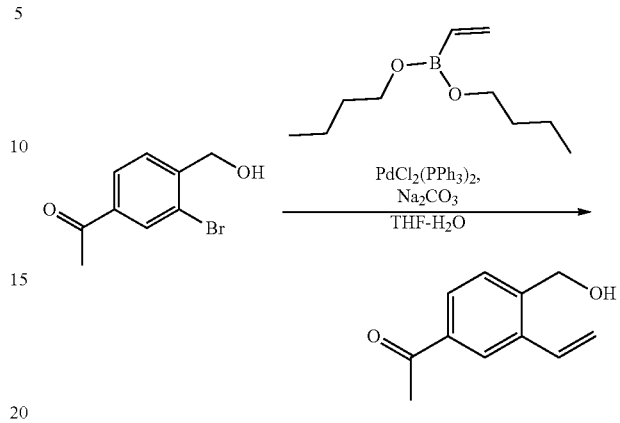

1-(3-bromo-4-(hydroxymethyl)phenyl)ethan-1-one (100 g) and THF (3 L) were charged in clean and dry RBF equipped with reflux condenser and guard tube at 28° C. Dibutyl vinyl borate (144.64 g) and 2M aqueous sodium carbonate solution (323.87 g) were added. The reaction mass was purged with nitrogen gas for 30 minutes. $PdCl_2(PPh_3)_2$ (15.32 g) was added to the reaction mass at 29° C. The reaction mixture was heated to 80° C. and stirred for 10 hours. The reaction mass was cooled to 28° C. and extracted with ethylacetate (3×500 mL). Organic layer was washed with water (500 mL) and brine (800 mL). The organic layer was dried over sodium sulfate and concentrated under reduced pressure at 45° C. to yield 120 g of pale colored syrup. Purity: 75.95%.

Example-11(c): Preparation of 1-(3-ethyl-4-(hydroxymethyl)phenyl)ethan-1-one (Compound of Formula XII)

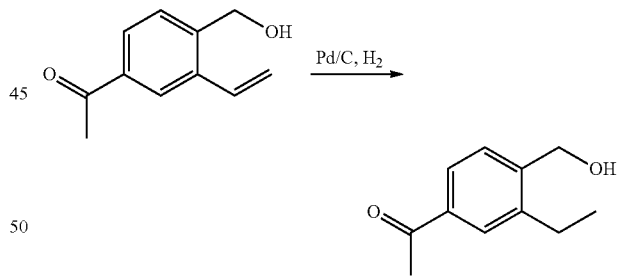

Crude 1-(4-(hydroxymethyl)-3-vinylphenyl)ethan-1-one (126 g) and methanol (1512 mL) were charged into a hydrogenation vessel at 29° C. 5% Pd/C (50% wet, 50.4 g) was added and hydrogen gas applied. The hydrogen gas was maintained at 15 psi for 4 hours at 28° C. The reaction mixture was filtered through a celite bed and the bed was washed with methanol (500 mL). The filtrate was concentrated under reduced pressure at 45° C. and the resulting crude compound was purified by silica gel (60-120 mesh) column chromatography and compound was eluted in 15-20% EtOAc/Hexane. The fractions containing the compound were combined and concentrated under reduced pressure at 45° C. to yield 82.8 g of the compound of formula XII as light yellow syrup. Purity: 90.67%.

Example-12: Alternate method for preparation of 1-(3-ethyl-4-(hydroxymethyl)phenyl)ethan-1-one (Compound of Formula XII)

Example-12(a): Preparation of 1-(3-bromo-4-(((tert-butyldimethylsilyl)oxy)methyl)phenyl)ethan-1-one

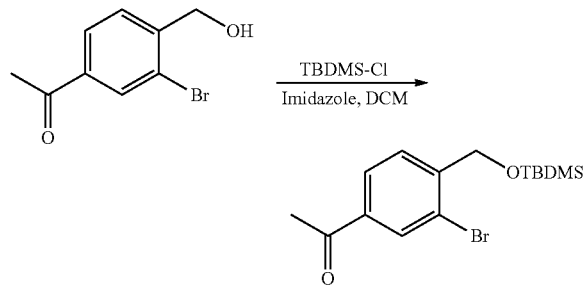

1-(3-bromo-4-(hydroxymethyl)phenyl)ethan-1-one (5 g) and DCM (50 mL) were charged into a 100 mL RBF equipped with nitrogen gas at room temperature and the mixture was cooled to 7° C. Imidazole (2.98 g) and TBDMSCl (5.14 g) were added to the reaction mixture. The resulting reaction mixture was stirred for 2 hours at 28° C. Water (50 mL) was added to the reaction mass and stirred for 10 minutes. Layers separated and the organic layer was further washed with water (2×50 mL) and brine (50 mL) solution. The organic layer was dried over sodium sulphate and concentrated under reduced pressure below 50° C. to yield 6.5 g of title compound as light brown color syrup. Purity: 67.99%

Example-12(b): Preparation of 1-(4-(((tert-butyldimethylsilyl)oxy)methyl)-3-vinylphenyl)ethan-1-one

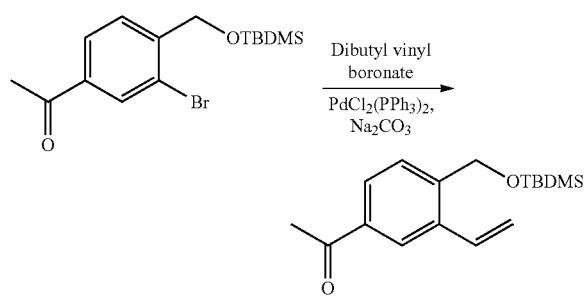

1-(3-bromo-4-(((tert-butyldimethylsilyl)oxy)methyl)phenyl)ethan-1-one (6 g) and THF (180 mL) were charged into a 500 mL clean and dry RBF equipped with reflux condenser and guard tube at 28° C. Dibutyl vinyl borate (5.78 g) and 2.0M aqueous sodium carbonate solution (12.96 g) were added. The reaction mass was purged with nitrogen gas for 30 minutes. $PdCl_2(PPh_3)_2$ (0.613 g) was added to the reaction mass at 29° C. The reaction mixture was heated to 80° C. and stirred for 9 hours. The reaction mass was cooled to 28° C. and extracted with ethylacetate (2×30 mL). Organic layer was washed with water (30 mL) and brine (30 mL). The organic layer was dried over sodium sulfate and concentrated under reduced pressure at 45° C. to yield 5.3 g of light brown colored syrup. Purity: 59.27%.

Example-12(c): Preparation of 1-(3-ethyl-4-(hydroxymethyl)phenyl)ethan-1-one (Compound of Formula XII)

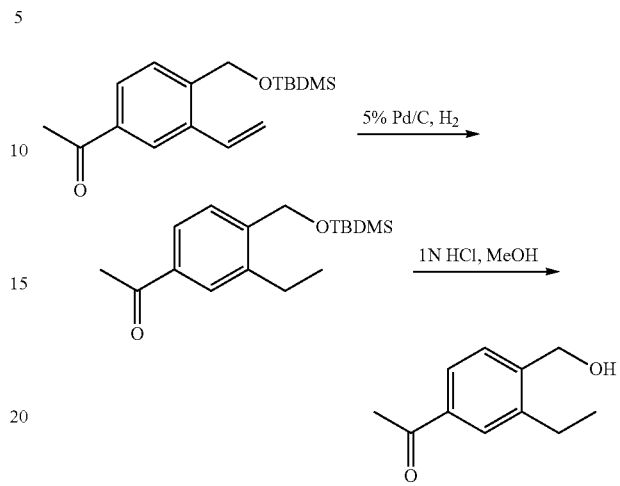

1-(4-(((tert-butyldimethylsilyl)oxy)methyl)-3-vinylphenyl)ethan-1-one (5.0 g) and methanol 25 mL) were charged into a 250 mL hydrogenation vessel at room temperature at 29° C. 5% Pd/C (50% wet, 1.0 g) was added and hydrogen gas applied. The hydrogen gas was maintained at 20 psi for 3 hours at 28° C. The reaction mixture was filtered through a celite bed and the bed was washed with methanol (20 mL). The filtrate was concentrated under reduced pressure at 45° C. and the resulting crude compound was diluted with methanol (25 mL) and 1N HCl (10 mL) at 28° C. The mixture was stirred at 28° C. for 20 minutes. The reaction mixture was concentrated under reduced pressure at 45° C. The resulting crude compound was purified by silica gel (60-120 mesh) column chromatography and compound was eluted in 20-25% EtOAc/Hexane. The fractions containing the compound were combined and concentrated under reduced pressure below 50° C. to yield 1.4 g of the compound of formula XII as light yellow syrup. Purity: 83.51%.

Example-13: Preparation of Amorphous Siponimod Hemifumarate

Figure 2:
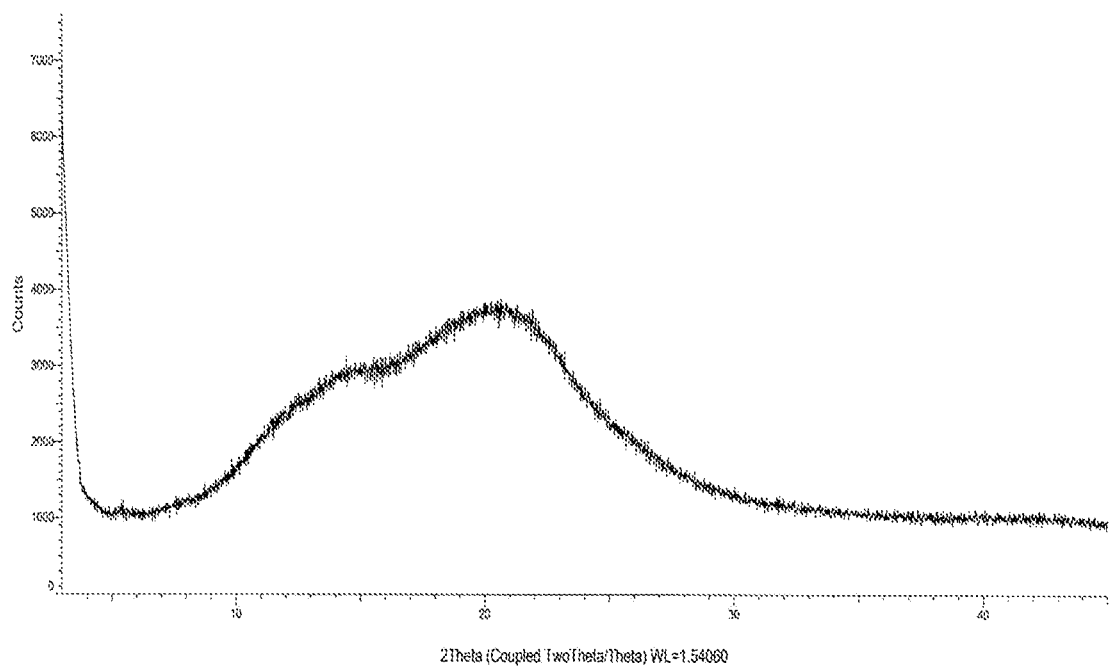
FIG. 2 is powder X-ray power diffraction ("PXRD") pattern of an amorphous form of Siponimod hemifumarate prepared according to Example 13.

Siponimod hemifumarate (4.0 g) and methanol (200 mL) were charged into a 500 mL rotavapor flask. The mixture was heated to 66° C. under stirring, and the clear solution was concentrated under vacuum at 66° C. to yield 2.5 g of amorphous Siponimod hemifumarate. PXRD as shown in FIG. 2.

Figure 3:
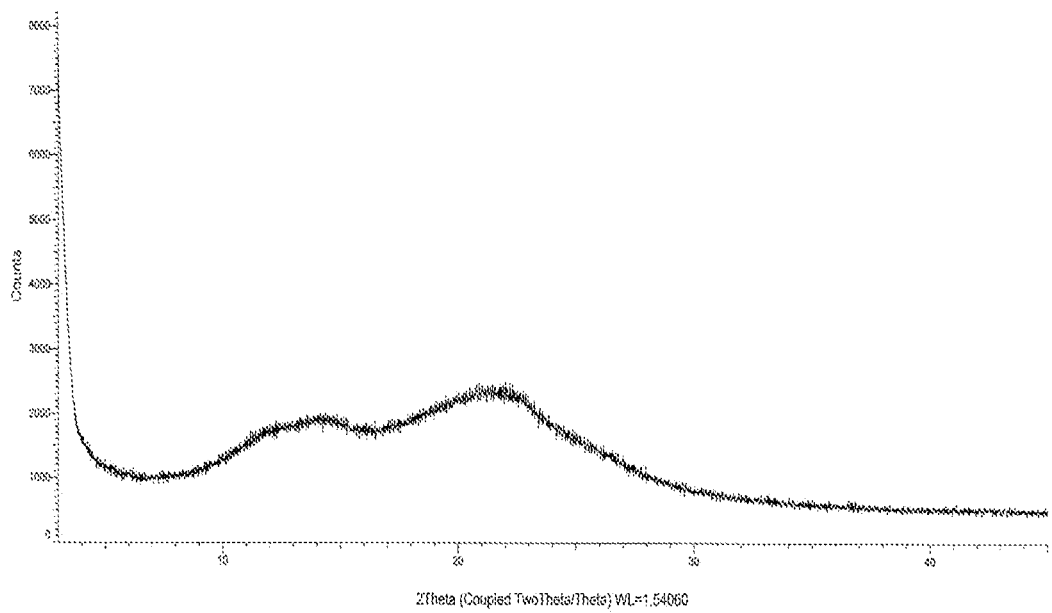
FIG. 3 is powder X-ray power diffraction pattern of amorphous solid dispersion comprising Siponimod hemifumarate and Syloid (1:0.5 w/w) prepared according to Example 13.

The amorphous Siponimod hemifumarate (1.0 g) and Syloid (0.5 g) were mixed in a rotavapor flask (rpm of rotavapor is 40) for 30 minutes. The resulted solid was isolated and analyzed. PXRD of the resulted solid is shown in FIG. 3.

Example-14: Preparation of Amorphous Solid Dispersion of Siponimod Hemifumarate and Hydroxy Propyl Methyl Cellulose (HPMC)

Figure 4:
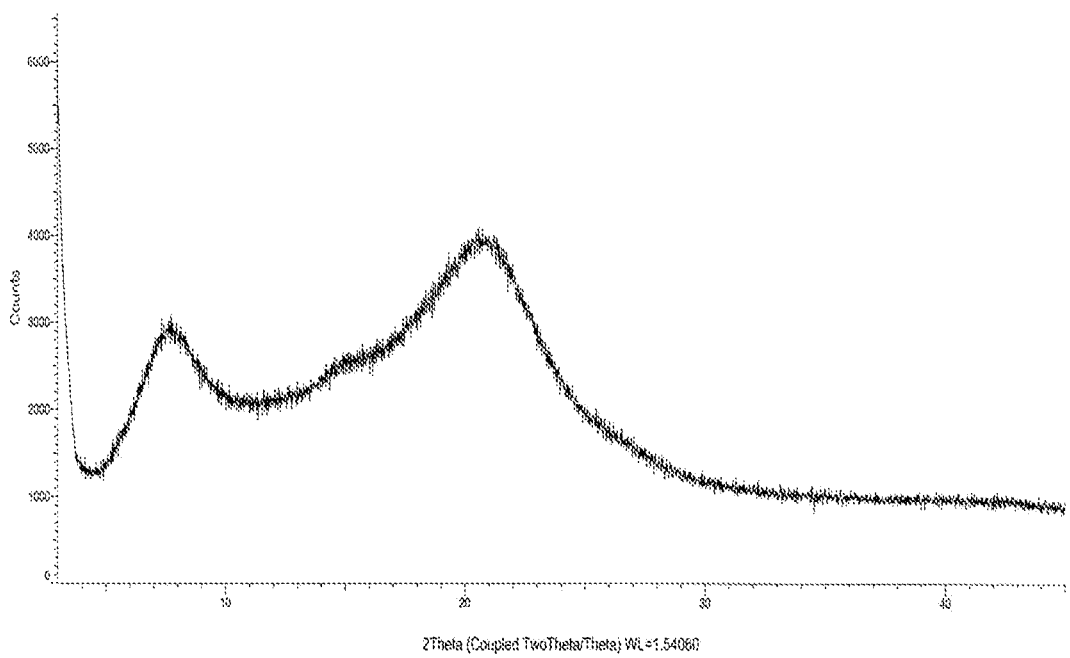
FIG. 4 is powder X-ray power diffraction pattern of amorphous solid dispersion comprising Siponimod hemifumarate and hydroxypropyl methyl cellulose (HPMC) (1:1 w/w) prepared according to Example 14.

Siponimod hemifumarate (1.5 g), methanol (100 mL) and Hydroxy propyl methyl cellulose (HPMC, 1.5 g) were charged into a 500 mL rotavapor flask at 27° C. The resulted mixture was heated to 65° C. and stirred for 10 min. at 65° C. The heterogeneous mixture was completely evaporated under reduced pressure at 65° C. To the solid added a mixture of dichloromethane and methanol (50 mL of dichloromethane and 100 mL of methanol) and heated to 65° C. The resulted gel like material was concentrated under reduced pressure at 65° C. 1.7 g of flakes like material was obtained. PXRD pattern: FIG. 4.

Example 15: Preparation of Amorphous Solid Dispersion of Siponimod Hemifumarate and Polyvinylpyrrolidone K-30 (PVP K-30)

Figure 5:
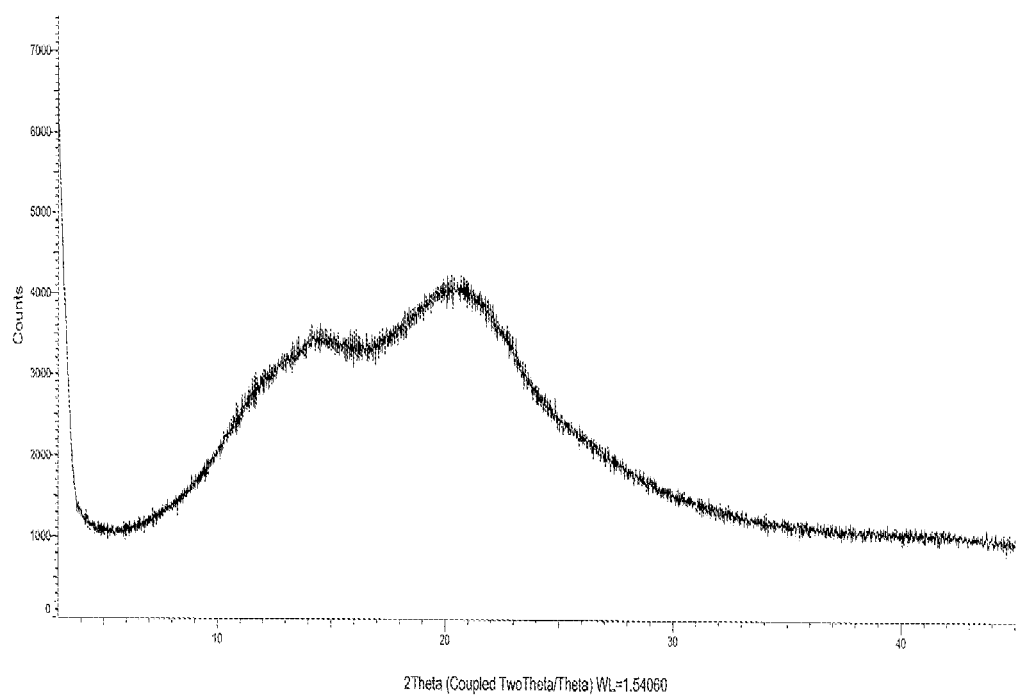
FIG. 5 is powder X-ray power diffraction pattern of amorphous solid dispersion comprising Siponimod hemifumarate and Polyvinylpyrrolidone K-30 (PVP K-30) (1:1 w/w) prepared according to Example 15.

Siponimod hemifumarate (1.5 g), Polyvinylpyrrolidone K-30 (PVP K-30, 1.5 g), and methanol (100 mL) were charged into a 500 mL rotavapor flask at 27° C. The mixture was heated to 65° C. and stirred for 5 min. at 65° C. The resulted clear solution was concentrated under reduced pressure at 65° C. The material was dried at 65° C. under reduced pressure. 2.1 g of amorphous solid dispersion was obtained. PXRD pattern: FIG. 5.

Example-16: Preparation of Di-p-Toluolyl-L-Tartaric Acid Salt of Siponimod

Siponimod (2.0 g) and ethanol (20 mL) were charged into a 250 mL round bottom flask at 25° C. Di-p-toluolyl-L-tartaric acid (1.497 g) was added at 25° C. and the mixture was stirred for 20 minutes. The reaction mixture was concentrated under reduced pressure at 45° C. To the residue acetonitrile (40 mL) was charged and the mixture was stirred at 25° C. for 6 hours. The precipitation was filtered and the solid was washed with acetonitrile (10 mL). The solid was dried in a hot air oven at 50° C. to yield 2.80 g of crystalline Siponimod Di-p-toluolyl-L-tartrate.
PXRD pattern: FIG. 6. Purity: 98.8% by HPLC.

Example-17: Preparation of Di-Benzoyl-D-Tartaric Acid Salt of Siponimod

Siponimod (2.0 g) and ethanol (20 mL) were charged into a 250 mL round bottom flask at 25° C. Di-Benzoyl-D-tartaric acid (1.388 g) was added at 25° C. and the mixture was stirred for 20 minutes. The reaction mixture was concentrated under reduced pressure at 45° C. To the residue acetonitrile (40 mL) was charged and the mixture was stirred at 25° C. for 6 hours. The precipitation was filtered and the solid was washed with acetonitrile (10 mL). The solid was dried in a hot air oven at 40° C. to yield 2.70 g of crystalline Siponimod Di-Benzoyl-D-tartrate.
PXRD pattern: FIG. 7. Purity: 97.0% by HPLC.

Example-18: Preparation of Isethionic Acid Salt of Siponimod

Figure 8:
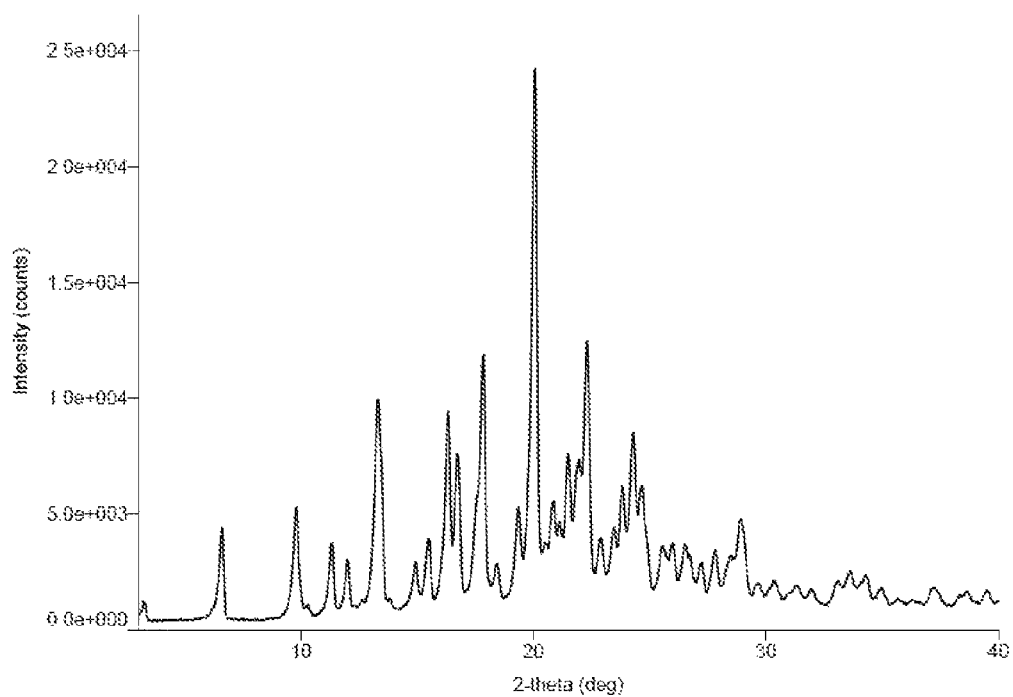
FIG. 8 is powder X-ray diffraction pattern of Siponimod isethionate prepared according to Example 18.

Siponimod (2.0 g) and ethanol (20 mL) were charged into a 250 mL round bottom flask at 25° C. Isethionic acid (0.488 g) was added at 25° C. and the mixture was stirred for 20 minutes. The reaction mixture was concentrated under reduced pressure at 45° C. To the residue acetonitrile (40 mL) was charged and the mixture was stirred for at 25° C. for 6 hours. The mixture was concentrated under reduced pressure at 45° C. To the residue ethylacetate (40 mL) was charged and the mixture was stirred at 25° C. for 6 hours. The precipitation was filtered and the solid was dried under vacuum at 25° C. to yield 1.50 g of crystalline Siponimod isethionate. PXRD pattern: FIG. 8. Purity: 98.2% by HPLC.

Example-19: Preparation of Crystalline Form SHF1 of Siponimod Hemifumarate

Amorphous siponimod hemifumarate (2.0 g) and water (6 mL) were charged into a 25 mL vial. The mixture was heated to 50° C. and stirred for 7 hours. The suspension was filtered and the wet solid was suction dried for 2 hours to yield 2 g of crystalline Form SHF1 of Siponimod hemifumarate. PXRD as shown in FIG. 9.

Example-20: Preparation of Crystalline Form SHF2 of Siponimod Hemifumarate

Amorphous siponimod hemifumarate (1.0 g) and 1,4-Dioxane (2 mL) were charged into a 10 mL vial and stirred for 10 hours. The suspension was filtered and the wet solid was dried under vacuum at 40° C. to yield 0.75 g of crystalline Form SHF2 of Siponimod hemifumarate. PXRD as shown in FIG. 10.

Example-21: Preparation of Crystalline Form SF1 of Siponimod Monofumarate

Siponimod base (100 mg), fumaric acid (22 mg) and ethylformate (1 mL) were charged into a 5 mL vial and stirred for 10 hours. The suspension was filtered and the wet solid was dried under vacuum at 40° C. to yield crystalline Form SF1 of Siponimod monofumarate. PXRD as shown in FIG. 11.

Example-22: Preparation of Amorphous Solid Dispersion of Siponimod Hemifumarate and Kollidon VA64 (1:1 w/w)

Figure 12:
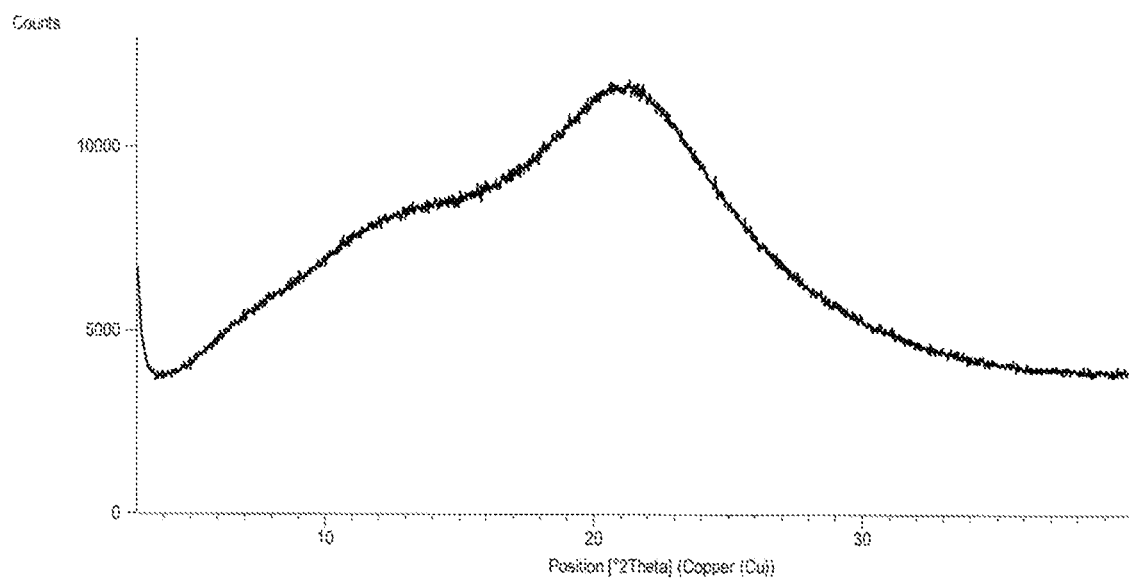
FIG. 12 is powder X-ray diffraction pattern of amorphous solid dispersion comprising Siponimod hemifumarate and Kollidon VA64 (1:1 w/w) prepared according to Example 22.

Kollidon VA64 (500 mg) and acetone (50 mL) were added to a 500 mL Buchi flask and stirred for 5 minutes. To the clear solution Siponimod hemifumarate (500 mg) and acetone (50 mL) were charged at 27° C. The Buchi flask containing the resulted mixture was kept for rotation and heated to 50° C. and stirred for 10 min. To the mixture methanol (10 mL) was added and stirred for 10 minutes at 50° C. The reaction mass was completely evaporated under reduced pressure at 50° C. 800 mg of solid material was obtained. PXRD pattern: FIG. 12.

Example 23: Preparation of Amorphous Solid Dispersion of Siponimod Hemifumarate and Kollidon VA64 (1:2 w/w)

Figure 13:
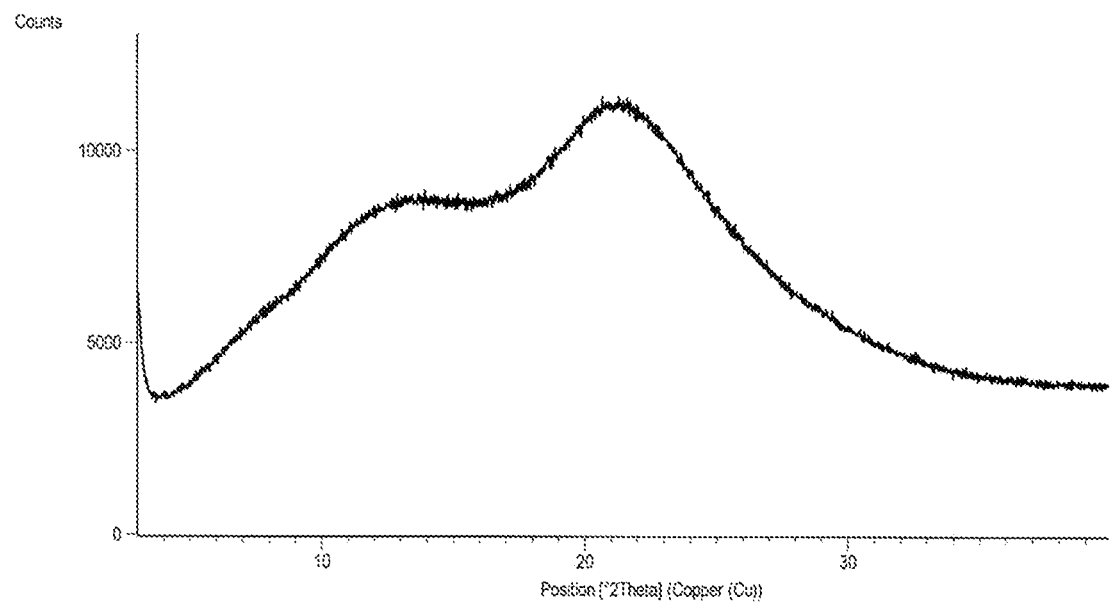
FIG. 13 is powder X-ray diffraction pattern of amorphous solid dispersion comprising Siponimod hemifumarate and Kollidon VA64 (1:2 w/w) prepared according to Example 23.
Figure 14:
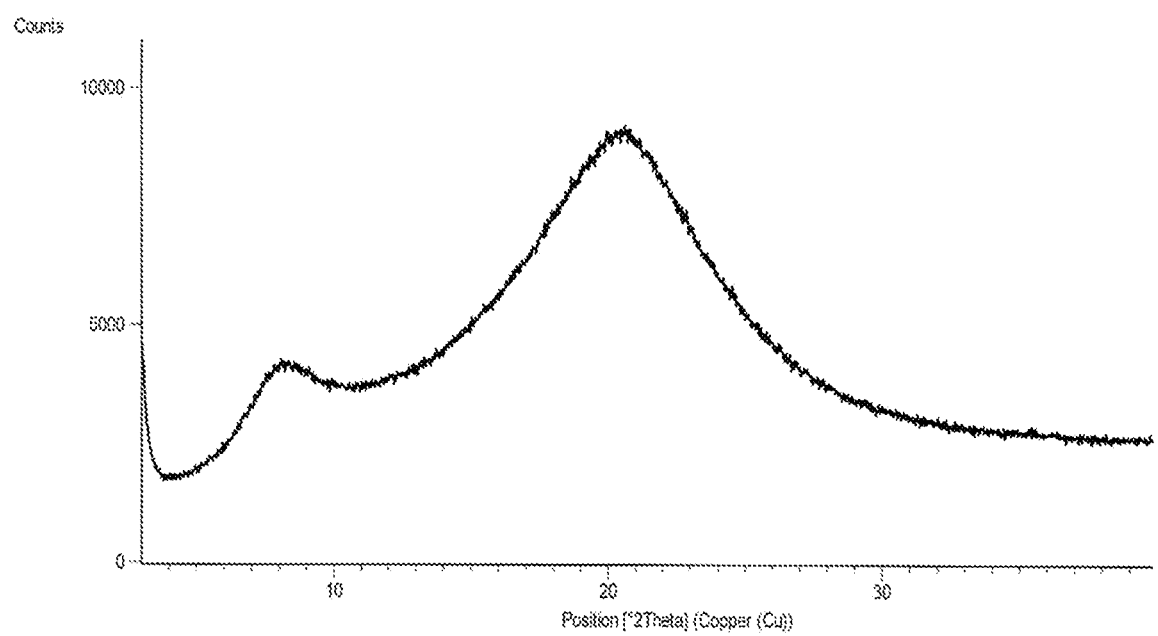
FIG. 14 is powder X-ray diffraction pattern of amorphous solid dispersion comprising Siponimod hemifumarate and Klucel LF (1:1 w/w) prepared according to Example 24.

Kollidon VA64 (1000 mg) and acetone (150 mL) were added to a 500 mL Buchi flask and stirred for 5 minutes. To the clear solution Siponimod hemifumarate (500 mg) was charged at 27° C. The Buchi flask containing the resulted mixture was kept for rotation and stirred for 10 min at 27° C. To the mixture methanol (15 mL) was added and stirred for 10 minutes. The reaction mass was completely evaporated under reduced pressure at 55° C. 1000 mg of solid material was obtained. PXRD pattern: FIG. 13.

Example 24: Preparation of Amorphous Solid Dispersion of Siponimod Hemifumarate and Klucel LF (1:1 w/w)

Klucel LF (500 mg) and acetone (50 mL) were added to a 500 mL Buchi flask and stirred for 5 minutes. To the clear solution Siponimod hemifumarate (500 mg) was charged at 27° C. The Buchi flask containing the resulted mixture was kept for rotation and stirred for 10 min. To the mixture methanol (50 mL) was added and stirred for 10 minutes. The reaction mass was completely evaporated under reduced pressure at 60° C. 750 mg of solid material was obtained. PXRD pattern: FIG. 4.

Example 25: Preparation of Amorphous Solid Dispersion of Siponimod Hemifumarate and Hydroxy Propyl Cellulose (HPC L) (1:1 w/w)

Figure 15:
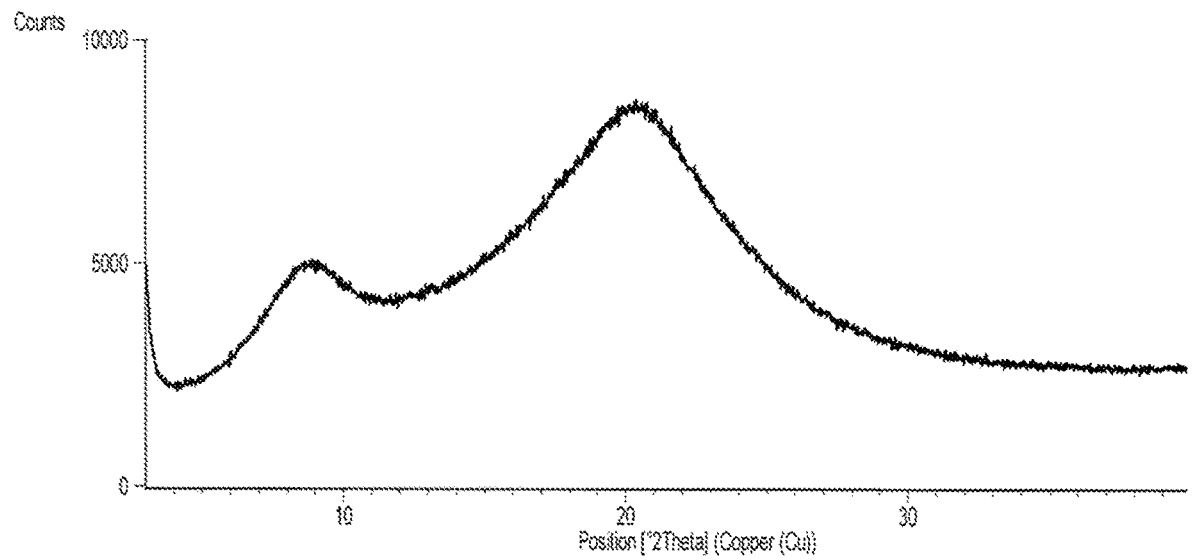
FIG. 15 is powder X-ray diffraction pattern of amorphous solid dispersion comprising Siponimod hemifumarate and hydroxypropyl cellulose (HPC L) (1:1 w/w) prepared according to Example 25.

Hydroxy Propyl Cellulose L (500 mg) and acetone (100 mL) were added to a 500 mL Buchi flask and stirred for 5 minutes. To the mixture Siponimod hemifumarate (500 mg) and methanol (10 mL) were charged at 27° C. The Buchi flask containing the resulted mixture was kept for rotation and stirred for 20 min at 50° C. The clear solution obtained was completely evaporated under reduced pressure at 55° C. 700 mg of solid material was obtained. PXRD pattern: FIG. 15.

Example 26: Preparation of Amorphous Solid Dispersion of Siponimod Hemifumarate and Soluplus (1:3 w/w)

Figure 16:
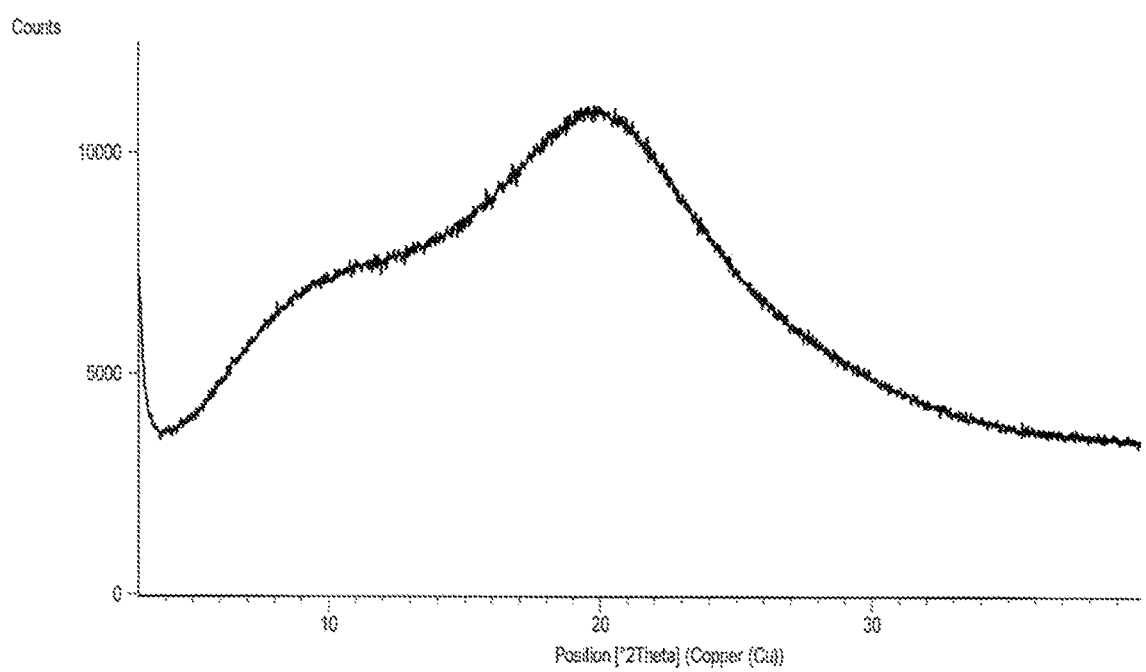
FIG. 16 is powder X-ray diffraction pattern of amorphous solid dispersion comprising Siponimod hemifumarate and Soluplus (1:3 w/w) prepared according to Example 26.

Soluplus (1500 mg) and methanol (100 mL) were added to a 500 mL Buchi flask and stirred for 5 minutes. To the mixture Siponimod hemifumarate (500 mg) was added at 27° C. The Buchi flask containing the resulted mixture was kept for rotation and stirred for 20 min at 60° C. The clear solution obtained was completely evaporated under reduced pressure at 65° C. 1400 mg of solid material was obtained. PXRD pattern: FIG. 16.

Example 27: Preparation of Amorphous Solid Dispersion of Siponimod Hemifumarate and Soluplus (1:2 w/w)

Figure 17:
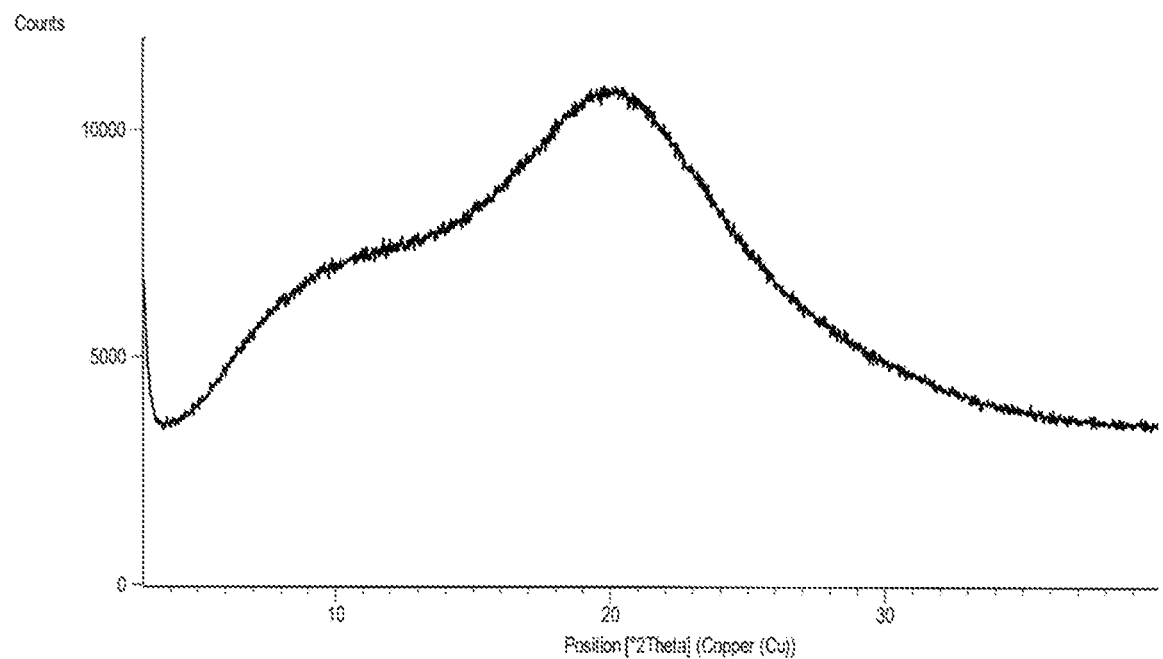
FIG. 17 is powder X-ray diffraction pattern of amorphous solid dispersion comprising Siponimod hemifumarate and Soluplus (1:2 w/w) prepared according to Example 27.

Soluplus (1000 mg) and methanol (100 mL) were added to a 500 mL Buchi flask and stirred for 5 minutes. To the mixture Siponimod hemifumarate (500 mg) was added at 27° C. The Buchi flask containing the resulted mixture was kept for rotation and stirred for 20 min at 60° C. The clear solution obtained was completely evaporated under reduced pressure at 65° C. 1000 mg of solid material was obtained. PXRD pattern: FIG. 17.

Example 28: Preparation of Amorphous Solid Dispersion of Siponimod Hemifumarate and Soluplus (1:1 w/w)

Figure 18:
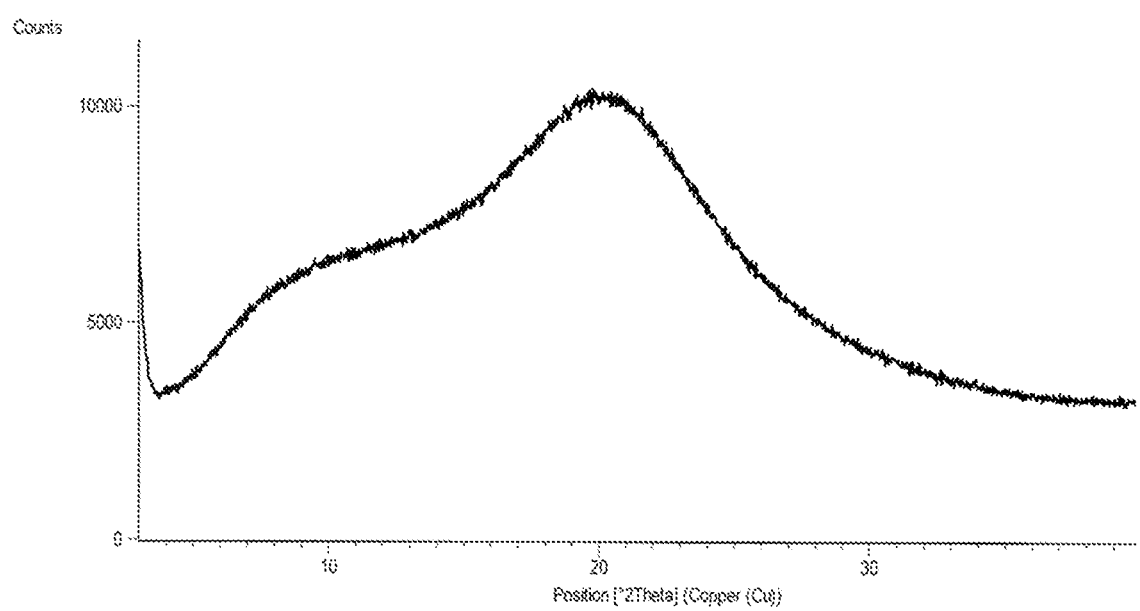
FIG. 18 is powder X-ray diffraction pattern of amorphous solid dispersion comprising Siponimod hemifumarate and Soluplus (1:1 w/w) prepared according to Example 28.

Soluplus (500 mg) and methanol (50 mL) were added to a 500 mL Buchi flask and stirred for 5 minutes. To the mixture Siponimod hemifumarate (500 mg) was added at 27° C. The Buchi flask containing the resulted mixture was kept for rotation and stirred for 20 min at 60° C. The clear solution obtained was completely evaporated under reduced pressure at 65° C. 600 mg of solid material was obtained. PXRD pattern: FIG. 18.

Example-29: Preparation of Crystalline Form SHF1 of Siponimod Hemifumarate

Siponimod hemifumarate (600 mg) and water (24 mL) were charged into a 100 mL vial. The mixture was heated to 75° C. and added acetonitrile (8 mL) and stirred for 30 minutes. The clear solution obtained was cooled to 3° C. and stirred for 90 minutes. The suspension obtained was filtered and the wet solid was dried for 1 hour using a vacuum tray dryer (VTD) to yield 300 mg of crystalline Form SHF1 of Siponimod hemifumarate. PXRD as shown in FIG. 9.

Example-30: Preparation of Siponimod Hemifumarate L-Proline (1:1) Co-Crystal

Figure 19:
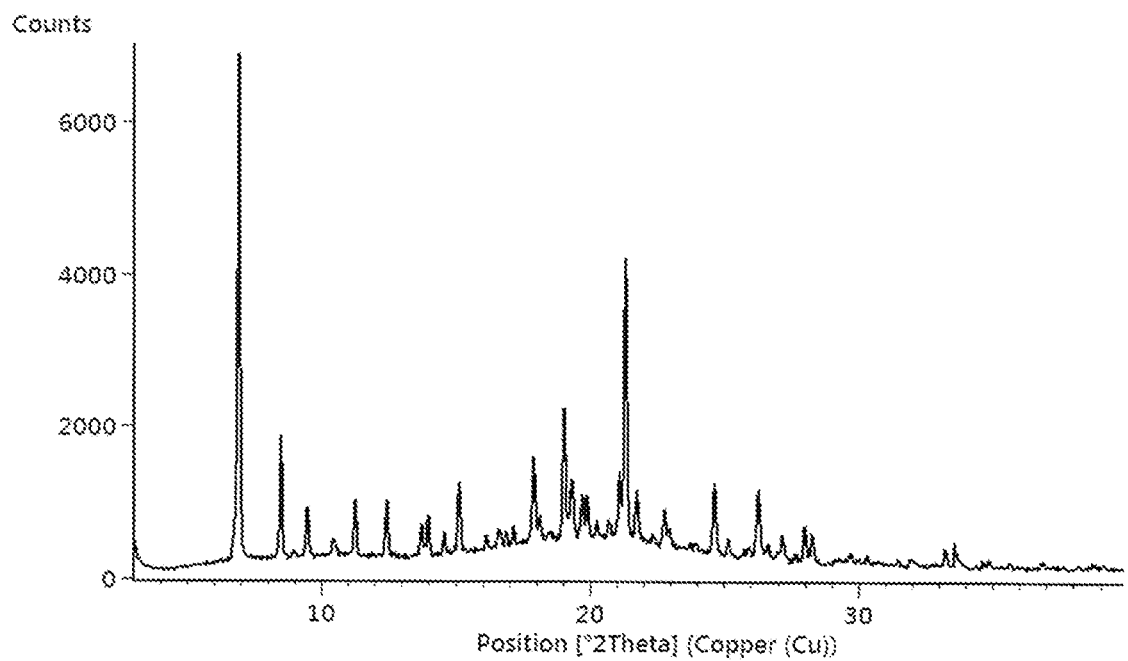
FIG. 19 is powder X-ray diffraction pattern of crystalline form of Siponimod hemifumarate L-proline co-crystal (SLP) prepared according to Example 30.

Siponimod base (100 mg), fumaric acid (11 mg), L-proline (22.2 mg) and methanol (5 mL) were charged into a 25 mL vial and stirred for 30 minutes. The mixture was heated to 60° C. and stirred for 7 hours. The mixture was cooled to 25° C. and stirred for 8 hours. The suspension was filtered and the wet cake was washed with n-heptane (5 mL). The wet solid was dried under vacuum at 40° C. to yield crystalline Siponimod hemifumarate L-proline complex (Form SLP).
PXRD as shown in FIG. 19.

Example-31: Preparation of Crystalline Siponimod Base Form S

Figure 20:
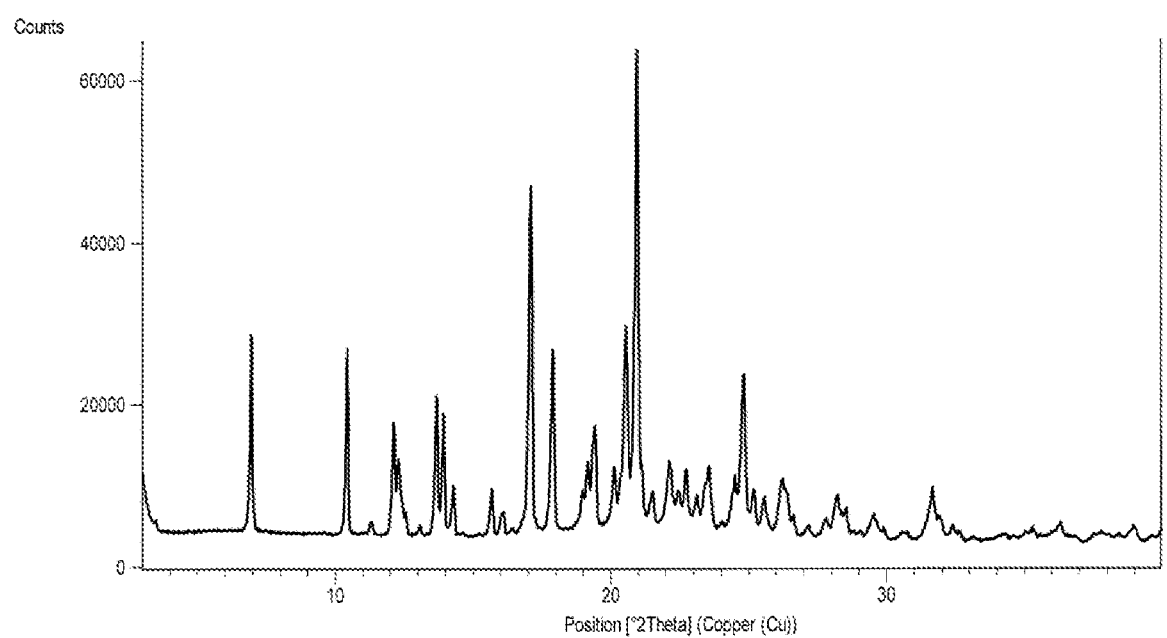
FIG. 20 is powder X-ray diffraction ("PXRD") pattern of crystalline form S of Siponimod base prepared according to Example 32.

Glycerin (20 mL) was added to a crystallization vessel and heated to 75° C. Siponimod hemifumarate (500 mg) was added to the hot glycerin and stirred for 5 hours at 75° C. Glycerin (10 mL) was added to the mixture and cooled to 65° C. and methanol (25 mL) was added and the mixture was stirred for 2 hours at 65° C. to get clear solution. The solution was cooled to 0° C. and stirred for 10 hours. The mixture was left two days for slow evaporation at 27° C. The suspension was filtered under vacuum and sucked to dry at 27° C. PXRD as shown in FIG. 20.

Example-32: Preparation of Crystalline Siponimod Base Form S

Glycerin (225 mL) was added to a crystallization vessel and heated to 85° C. Siponimod hemifumarate (5 g) was added to the hot glycerin and stirred for 1 hour at 85° C. The mixture was cooled to 65° C. and methanol (150 mL) was added and the mixture was stirred for 2 hours at 65° C. Glycerin (15 mL) and methanol (10 mL) were added to the mixture and stirred for 1 hour at 65° C. to get clear solution. The solution was cooled to 30° C. and transferred to another crystallization vessel. The mixture was left four days for slow evaporation at 27° C. The suspension was filtered under vacuum and the wet material was washed with MTBE (150 mL) and sucked to dry at 27° C. The wet material was washed again with MTBE (150 mL) and sucked to dry at 27° C. The material was dried in VTD at 40° C.
PXRD matches with FIG. 20.

Example-33: Preparation of Amorphous Siponimod Hemifumarate

Siponimod hemifumarate (6.0 g) and methanol (350 mL) were charged into a 1000 mL rotavapor flask. The mixture was heated to 45° C. under rotation, and the clear solution was filtered under vacuum. The clear solution was concentrated under vacuum at 46° C. and the solid obtained was dried under vacuum to yield 5.2 g of amorphous Siponimod hemifumarate. PXRD as shown in FIG. 2.

Example-34: Preparation of Crystalline Form SHF1 of Siponimod Hemifumarate

Siponimod hemifumarate (3.0 g) and water (120 mL) were charged into a 500 mL crystallization flask. The mixture was heated to 50° C. and stirred for 30 minutes. Acetonitrile (40 mL) was added to the mixture and heated to 75° C. and stirred for 30 minutes. The resulted solution was gradually cooled to 5° C. and stirred for 1 hour at 5° C. The suspension was filtered and the wet solid was suction dried for 2 hours to yield 2 g of crystalline solid. The wet solid was divided into two portions as Part-A and part-B. The part-A portion was dried under ATD at 45° C. for 1 hour. The part-B portion was dried under VTD at 45° C. for 1 hour. PXRD of both the portions is same and is shown in FIG. 9.

Example-35: Preparation of Crystalline Form SHF2 of Siponimod Hemifumarate

Siponimod hemifumarate (7.5 g) and 1,4-Dioxane (130 mL) were charged into a 500 mL crystallization flask and the mixture was heated to 75° C. and stirred for 15 minutes. The clear solution was filtered at 50° C. and quickly transferred into another crystallization flask. The solution was stirred for 15 minutes at 75° C. and gradually cooled to 25° C. over a period of 3 hours. The suspension was filtered and the wet solid was suction dried for 1 hour to yield 6.5 g of crystalline Form SHF2 of Siponimod hemifumarate. PXRD as shown in FIG. 10.

The invention claimed is:
1. Amorphous form of Siponimod hemifumarate.
2. The amorphous form of Siponimod hemifumarate of claim 1 is characterized by powder X-ray diffraction (PXRD) substantially as illustrated in FIG. 1 or FIG. 2.
3. A process for preparing amorphous form of Siponimod hemifumarate of claim 1, comprising;
    (a) providing a solution of Siponimod hemifumarate in a solvent or a mixture of two or more solvents;
    (b) removing solvent from the solution of Siponimod hemifumarate obtained in step a); and
    (c) recovering amorphous form of Siponimod hemifumarate.
4. The process according to claim 3, wherein the solvent used in step (a) is selected from the group comprising methanol, ethanol, isopropyl alcohol, dichloromethane.
5. The process according to claim 3, wherein the solvent used in step (a) is methanol.
6. The process according to claim 3, wherein the solvent used in step (a) is a mixture of methanol and dichloromethane.
7. A pharmaceutical composition comprising amorphous Siponimod hemifumarate of claim 1 and one or more pharmaceutically acceptable excipients.

* * * * *